(12) United States Patent
Dubrovsky

(10) Patent No.: US 8,343,172 B2
(45) Date of Patent: Jan. 1, 2013

(54) SEWING DEVICE FOR MAKING A MECHANICAL ENCIRCLING STITCH

(76) Inventor: Arkady Veniaminovich Dubrovsky, Moscow (RU)

( * ) Notice: Subject to any disclaimer, the term of this patent is extended or adjusted under 35 U.S.C. 154(b) by 370 days.

(21) Appl. No.: 12/595,251

(22) PCT Filed: Jan. 16, 2008

(86) PCT No.: PCT/RU2008/000015
§ 371 (c)(1),
(2), (4) Date: Oct. 9, 2009

(87) PCT Pub. No.: WO2008/127149
PCT Pub. Date: Oct. 23, 2008

(65) Prior Publication Data
US 2010/0114122 A1 May 6, 2010

(30) Foreign Application Priority Data

Apr. 11, 2007 (RU) ................................ 2007113416

(51) Int. Cl.
*A61B 17/04* (2006.01)
(52) U.S. Cl. ........................................ 606/144; 606/148
(58) Field of Classification Search ................... 606/139, 606/148, 222, 205–207, 210, 232, 233, 144
See application file for complete search history.

(56) References Cited

U.S. PATENT DOCUMENTS 4,557,265 A   12/1985  Andersson
7,361,180 B2 *  4/2008  Saadat et al. ................... 606/139

FOREIGN PATENT DOCUMENTS

| RU | 2 106 816 | 3/1998 |
| RU | 2 119 771 | 10/1998 |
| RU | 2 284 160 | 2/2004 |
| SU | 715082 | 2/1980 |

OTHER PUBLICATIONS

English Abstract of RU 2119771 dated Oct. 10, 1998.
Partial English translation of SU 715082 dated Feb. 25, 1980.
English Abstract of RU 2 106 816 dated Mar. 20, 1998.
English Abstract of RU 2284160 dated Feb. 10, 2004.

* cited by examiner

*Primary Examiner* — Julian Woo
(74) *Attorney, Agent, or Firm* — Ladas & Parry LLP

(57) ABSTRACT

The inventive sewing device for overcasting a mechanical twisted suture comprises a body (1) provided with a spiral needle (12) which is rotatable and translationally displaceable and is connected to a drive for rotating it, clamping jaws (6, 7) which are arranged on the distal end of the body for fixing the tissue parts to be sewed and provided with a unit for controlling the relative position thereof. The spiral needle (12) is designed in the form of an atraumatic or a hollow needle, is provided with a thread arranged therein, comprises at least two complete turns and is positioned in such a way that it is displaceable in a direction along the clamping jaws (6, 7) at a distance equal to or greater than the entire length of the spiral. The device comprises a nest (17) for catching the pointed end of the needle and/or the thread at the end of the suture and means for extracting the needle from the tissue. Said device makes it possible to reduce the trauma of sewed biological tissue, to improve the quality of the applied suture and to increase the operational reliability of the device by excluding failures in the needle displacement.

15 Claims, 17 Drawing Sheets

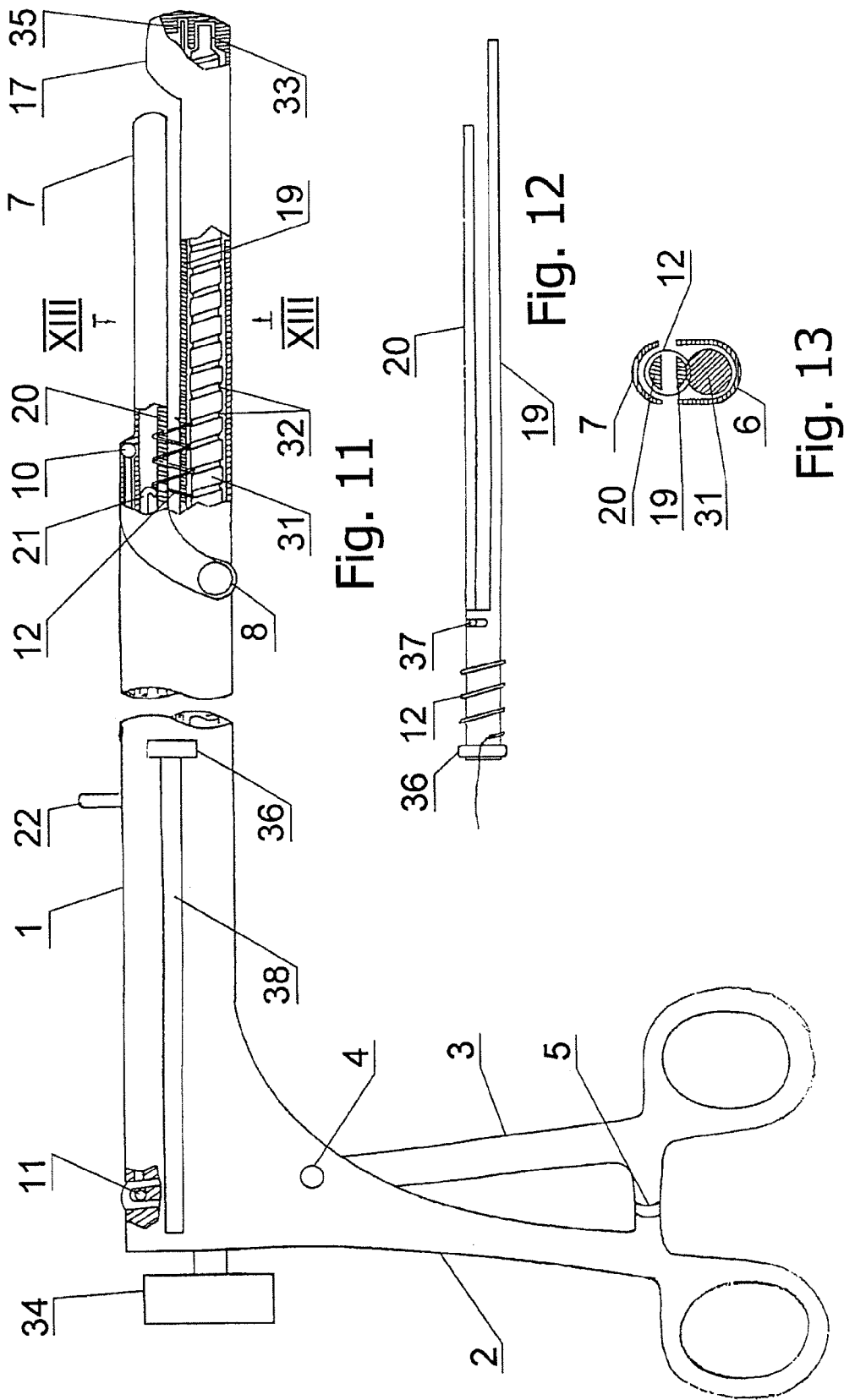

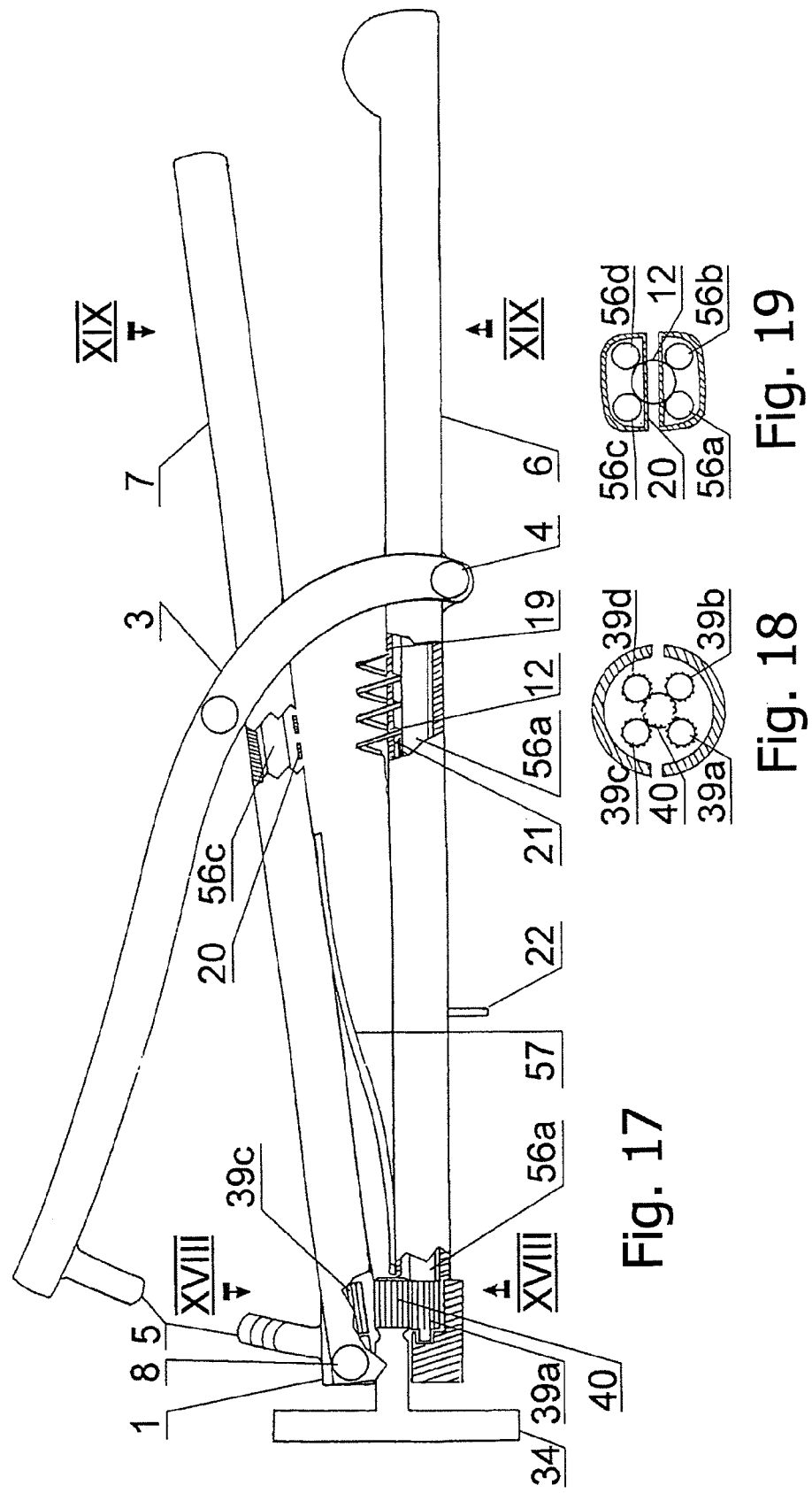

SEWING DEVICE FOR MAKING A MECHANICAL ENCIRCLING STITCH

FIELD OF THE INVENTION

The invention is related to medical instruments; more precisely, it concerns the sewing device for mechanical twining round stitches suture on biological tissues and is intended for use in various areas of surgery and in veterinary science, but can be used for sewing together tissues in other areas.

BACKGROUND OF THE INVENTION

The manual twining round stitches for tissue connection is often applied in the surgical practice. This stitch creates optimum conditions for healing tissues than modern non traumatic needles, allowing reducing a trauma of stitched tissues to a minimum, are used. Besides, the conditions for the hermetically sewed surface are created.

However the manual suture is not always and not everywhere convenient, not always it is done in regular intervals, demands the certain skills and suture of such stitches takes certain time. Therefore attempts to create the device for mechanical performance of a twining round stitches were repeatedly undertaken.

The sewing device for overcastting a mechanical twisted suture, containing a body and inside the body a deformable screw sewing element connected with a rotor in the form of a metal cylindrical spring, is known (RU 2106816 C1).

During sewing together, the sewing element screw in a tissue, stitching it on all thickness and for all length of a stitches. The deformation of the spires of a screw sewing element is used for the achievement of demanded tightness of the stitches.

However the use of this device, as well as the use of widely known devices sewing with the help of metal brackets, leads to the placement in the stitched tissues of a foreign body—a metal screw sewing element—a rigid foreign construction of the certain extent which can disturb the functions of the sewed organ.

It is known, besides, the sewing device putting in mechanical twining round stitches using an atraumatic spiral needle with a sewing thread fixed by its end on the blunt end of the needle (see RU 2119771 C1). In the given device as a sewing element are used the modern threads, including the threads dissolving by the time fixed.

This device contains the body with established possibility of rotation and forward moving by the spiral needle connected with a drive of its rotation; located on the distal end of the body tightening gripping jaws for fixing sewed sites of the tissue, supplied by the device managing their relative position.

The needle really executed in the form of one spiral coil (perimeter no more than 370°), is rotated by means of the leading and conducted rollers interacting with its lateral surface. When the suture is finished, the ends of the thread are cut with a specially intended knife. However the given device works unreliably, since a needle sometimes is slipping in the directing rollers, especially than sewing dense damp tissues.

To eliminate this problem, the needle with notches or hollows on its surface can be used, however this way leads to additional tissues trauma. Besides, the needle executed in the form of one coil of a spiral, has insufficiently rigid design and is subject to deformations when sewing a dense tissue that leads to decrease in quality of the suture.

SUMMARY OF THE INVENTION

The aim of the invention is to create a sewing device for overcasting a mechanical twisted suture with a spiral needle of such design which would both decrease the sewed tissue trauma and allow raising quality of the stitches, and also reliability of work of the device due to exception of failures in the movement of the needle.

To accomplish this aim a sewing device for overcasting a mechanical twisted suture has a body with a spiral needle, having a possibility of rotation and forward moving, connected with a drive of its rotation. The device also has on the distal end of the body tightening gripping jaws with handles managing their relative position; the spiral needle is an atraumatic one or a hollow spiral needle with the thread located in its cavity, contains at least two full coils and it is established with a possibility of moving on directing along tightening gripping jaws, at least for all length of a spiral, thus the device contains means for capture of the sharp end of a needle and-or a thread on the end of a stitches and means of taking out the needle from the tissue.

It is expedient, that means for capture of the sharp end of a needle and-or a threads represented a jack adapted for fixing of the sharp end of a spiral needle, established with a possibility of rotation on the distal end of one of tightening gripping jaws and connected with it by a demountable connection.

In a preferable variant of realization the distal end of a gripping jaws bearing a jack, is unbent, and on an internal surface of the second gripping jaws is executed a slant to direct the sharp end of a spiral needle to a jack.

In the first variant of realization the spiral needle is done with a lot of coils and contains such quantity of coils, that the length of a spiral exceeds length of the carried out twining round stitches.

Thus the external surface of tightening gripping jaws can be executed rounded for a possibility of the spiral needle sliding on an external surface of gripping jaws.

In one of variants of the realization the drive of the needle rotation can be executed in the form of the cylinder, established in the body with an opportunity of rotation with an internal thread in which cavity the spiral needle is located.

Besides, the drive of rotation can be connected with a needle by a demountable connection by means of flexible draft or a hinge rotary mechanism, preferably with a changeable angle of turn and adapted for selective connection with a needle at a stage of stitches or with a demountable jack at a stage of the needle getting out from a tissue.

The spiral atraumatic needle contains in the second variant of the realization 2-4 coils, and the drive of its rotation is done in the form of at least, one rotary roller which axis is parallel to an axis of a spiral and which cooperates by its lateral surface with a spiral with an opportunity of transmitting to it a rotary movement.

Thus it is expedient, that the device contains one or two rollers having a screw flute with step, equal or multiple to distance between coils of a spiral needle, or having on the surface the parallel cylindrical flutes, located one from another on the distance equal to distance between coils of a spiral needle.

It is also possible that the device will have three or four smooth rollers distributed on a circle of a spiral needle and having been drawn in to it.

In a preferable variant of the realization the drive of rotation of a jack for fixing the sharp end of a needle is located on a shaft, parallel to a longitudinal axis of a spiral needle and is connected with an external surface of a tooth gearing jack.

In case when the spiral needle is a hollow needle with the thread located in its cavity, the device is in addition supplied by the mechanism for taking out the thread after complete tissue sewing from the cavity of a spiral needle by mandrin, compressed air or a liquid and it's fixing in a jack.

Besides in case when the spiral needle is a hollow needle with a thread located in its cavity, the thread can be fixed in the sharp end of a needle, thus on the sharp end of a needle the weakened zone to divide the sharp end fixed in a jack with a thread from a body of a needle with a possibility of taking out the needle from the sewed tissue by reverse motion of a needle rotation drive is provided.

In variants of realization of the device when the spiral needle is an atraumatic needle, it is preferable to provide this device with the mechanism of taking out and tension of a thread through one, two or greater number of the atraumatic spiral needle turns.

The First Variant of the Sewing Device with Long Spiral Atraumatic Needle

Basis of this variant is atraumatic spiral needle with plural spires, i.e. the needle which is coming nearer on diameter to the diameter of pressed in its tail part of a thread, looks like a spiral with the certain radius of coils and the certain distance between coils of a spiral. The length of a spiral can be various and depends on length of carried out twining round stitches—preferably spiral needle contains such quantity of coils that the length of a spiral exceeds length of the carried out twining round stitches. Also the radius of coils of a spiral and distance between coils depending on thickness and properties of sewed tissues can be of various sizes.

The tail part of a spiral needle together with the pressed in it thread is densely inserted in the holder which is directly connected with a drive of the needle rotation. This holder can be simply dense emphasis for a tail part of a spiral needle and have its diameter or the possibility to clip a tail part of a spiral needle as a result of rapprochement of two parts of the holder, also not bigger on diameter than a spiral needle, can be stipulated. The holder of a tail part of a spiral needle can be also in the form of a corresponding collet clamp.

The drive of the device rotation can be executed, for example, in the form of the screw where the course of the spiral needle stitching tissues, is direct continuation of a course of the screwed screw in the handle of the device. However, instead of the screw, the simple core or the cylinder, on which distal end is strengthened the holder for a spiral needle can be used, since the spiral needle at rotation is screwed in the fixed tissues on directing according to the parameters.

As the source of rotation the adaptation for manual rotation or the electric motor of the minimal sizes can be used. Transfer of efforts from a source of rotation to a stitching spiral needle can be a straight line—on one shaft the drive of rotation and the holder of a tail part of a spiral needle settles down.

The drive of rotation can be connected also with a needle by a demountable connection by means of flexible draft in the form of a flexible rotating shaft or in the form of the hinge rotary mechanism, it is preferable with a changeable angle of the turn, transferring rotation under various angles, for example, through system of cardan joints or devices disclosed in RU 2284160 C2. In this case the drive of rotation can be executed with a possibility of selective connection with a needle at a stage of suture imposing or with a demountable jack at a stage of the needle taking out from the tissue.

Other variant of the mechanical device for screwing a spiral needle into stitched tissues is the hollow cylinder in which the spiral needle is located and which has an internal thread corresponding to the coils step of a spiral needle. This cylinder can be the same length as the spiral needle, but can be also short, for two-three coils of a spiral needle, and to settle down in the distal parts of the body before tightening working gripping jaws.

At rotation of this cylinder the spiral needle is screwed into a stitched tissue if its forward sharp end is already located in directing grooves of working gripping jaws. This moment will not allow the spiral needle to be scrolled freely together with the cylinder without progress. In the given variant the dimensions of the device are a little decreased.

The spiral needle moves following directing tightening gripping jaws fixing sewed tissues. The movement of a spiral needle is possible inside of tightening gripping jaws which are executed hollow, or on an external surface of gripping jaws which for this purpose are executed rounded.

In the first case the clip with gripping jaws is provided, each of which has inside a space necessary for accommodation and movement of a spiral needle half (on diameter). In the compressed condition both gripping jaws have inside a cavity in which all spiral needle is placed and moved.

The cavity in cross-section has an oval or coming nearer to oval form, its minimal internal diameter slightly exceeds diameter of a spiral needle, and the maximal diameter allows to place above and under a needle or on the one side of the needle a needle rotation drive, and also the mechanism of taking out and tension of the stitched thread. In this cavity the spiral needle moves, sewing the fixed tissues.

Sewed tissues should be squeezed relatively uniform on all length of a suture. Besides, it is necessary to create conditions for full sewing of the fixed tissues, i.e. at each coil the needle should rise above a surface of a sewed tissue. For this purpose on turned one to another parties of gripping jaws thin clamping plates with openings for pass of coils of a spiral needle and a thread following it are located in parallel each other. Superposed plates without openings are possible.

In this case the spiral needle rotates around these plates, and after the suturing, superposed plates are taken away, then a string is tightening.

The surface of the superposed plates can be covered by a thin film or a grid from a material biocompatible resolving or not resolving depending on tasks in view (for example, a grid from prolen, vicryl, hemostatic film, etc.) for maintenance of an additional hemostasis and for additional hermetic sealing of the suture.

In the second case, moving needle around of tightening gripping jaws is provided. This variant can be used also for imposing of the second suture row after suturing along the directing inside of gripping jaws.

In this case tightening gripping jaws should be thin enough and have the rounded external surface for a possibility of sliding of a spiral needle at screwing on an external surface of gripping jaws. In this variant the gripping jaws also should be removed before a tightening of the stitched thread.

On the distal end of one of tightening gripping jaws means for capture of the sharp end of a needle and-or a thread and taking out of a spiral needle from the stitched tissues is located. This means in a preferable variant of performance represents a jack in which the taking out from stitched tissues the front, sharp end of a spiral needle gets.

The jack is established on the distal end of one of gripping jaws with the possibility of rotation and is connected with it by a demountable connection. This jack can represent a cone or the cylinder with screw cutting on which the forward part of the spiral needle leaving stitched tissues is wound.

The cylinder can consist of two halves which at rapprochement compress the end of a spiral needle, or other variant of means of needle fixing, for example, a collet clamping device can be stipulated.

Taking out of a needle from tissues is made at rotation of the jack fixing the forward end of a spiral needle after its output from stitched tissues. This rotation can be made manually, but the mechanism of the rotation distal managements, for example, by means of a flexible rotating cable with the special cylinder which is put on a jack for fixing of the sharp end of a needle can be stipulated.

Tightening gripping jaws of the sewing device can be connected by the central hinge which can settle down both in the center of the case of the device, and in its proximal department. Other designs, allowing working gripping jaws to be rather parallel at fixing of tissue, can be used.

Considering the necessity of developing an internal space, relatively constant on all length of a gripping jaws, slightly exceeding external diameter of a spiral needle, the best variant is parallel or coming nearer to parallel arrangement of gripping jaws.

Edges of gripping jaws should not adjoin with each other for not admitting compressed tissues crushing. In modern standard devices sewing with clips the backlash between edges of gripping jaws can change from 1.0 up to 2.0 mm (devices UKL, companies USSC and Ethicon where the maximal size of clips reaches 4.0×4.5 mm).

Only in devices UDO-40 and UDO-60 where the largest clips 4.0×5.5 mm are used, the backlash can change from 1.5 up to 2.3 mm that is the extremely important in a lot of cases.

In described sewing devices for twinning round stitch suture thickness of a sewed tissue can be more, and the minimal size is not limited. The best variant is the use for tissues different on thickness different diameter of spiral needles.

The optimal maximal backlash between edges of gripping jaws can make one third of diameter of a needle spiral. For example, at a spiral needle with diameter of a spiral 6.0 mm the maximal thickness of a sewed fabric makes 2.0 mm, and at diameter of a spiral of 8.0 mm—it reaches 2.7 mm.

This is the essential difference from existing sewing devices with clips.

Tightening working gripping jaws of sewing devices can be absolutely direct, but the variant of gripping jaws with the certain curvature with the certain radius is possible, allowing the use of spiral needles.

The gripping jaws length in a preferable variant of realization corresponds to length of an imposed suture, but also can be less. In the latter case the possibility of consecutive tissue suture on the certain sites is provided. For this purpose one of gripping jaws is done more short, its internal edge is oblique for an output of not stitched part of soft tissues from gripping jaws. The spiral needle, continuing the way, gets on longer gripping jaw, on which distal end the jack for reception of the forward sharp end of a spiral needle is established.

The variant of realization of the sewing device in which the spiral needle leaves one of gripping jaws under some angle to a line of a seam at a direct arrangement of a stitched fabric is possible. In this case, the jack for reception of the sharp end of a needle settles down on unbent distal end of one gripping jaw, and on the end of the second gripping jaw on its internal surface is carried out slant for a direction of the sharp end of a spiral needle to a jack.

In all variants the thread drawing out mechanism during suturing after each coil of suturing is provided. Then using the thread with well polished surface facilitating sliding of the thread in tissues, it is possible to use the thread drawing out mechanism after two-three and more coils.

Fixing of the stitched thread can be carried out by various ways. It is possible to link the two ends of the stitched thread after its tension. It is possible to provide in advance the proximal end of a thread fixing on a teflon or other lining (it is better from a resolving material). In this case it is possible to fix only the distal end, for example, self-tightened threads which loop in advance is settled down at an output of the stitched threads from tissues.

It is possible to use self-fastened threads ("shrink-wrap" suture). It is possible to provide melting, pasting, pressing of the thread between corresponding planes, their jamming in a special crack, a twisting of the distal end of a thread in several planes on a teflon or resolving lining and so on.

The Second Variant of the Sewing Device with Short Spiral Atraumatic Needle

In this variant the spiral atraumatic needle with the length of two-four coils is used. For needle rotation and the tissue suturing, the various kinds of rollers operating movement of a spiral needle are used. The spiral needle, settled down with one part in a screw flute of a roller, is densely nestled on a demountable plate of a motionless gripping jaw. Rotation of a roller, in these conditions, forces rotation of the spiral needle.

In other variant of performance a roller one can have on the surface the parallel cylindrical flutes, located from another on distance equal to distance between coils of a spiral needle.

For more dense tissue, two rollers with a screw flute on the surface are provided, pressing the spiral needle from two sides. The variant of spiral needle pressing by three or four smooth rollers distributed on a circle of a spiral for reliable transfer of rotary movement to a spiral needle is possible.

The Third Variant of the Sewing Device with a Hollow Spiral Needle Having Plural Spires In this variant the hollow spiral needle which length is commensurable with the length of the suture is used. Two modifications of a hollow needle are possible.

In the first case inside of a hollow spiral needle the string which can be deduced from a needle under a pressure of air or a liquid, and also mandrin settles down. Practice shows, that for free sliding of the string inside of a spiral needle it is necessary to somehow increase internal diameter of a needle.

In the second case the thread, located in a hollow needle, is firmly fixed in the sharp end of a needle. Actually, in this variant a hollow needle and an atraumatic needle which is the sharp end of a hollow needle are combined. After tissue suturing the sharp end of a hollow needle gets in a jack for the sharp end of a needle, is fixed in it and is broken off on in advance stipulated weakened zone. Then the jack with the thread fixed in it is extended, and the remained part of a hollow needle is deduced from tissues at the return movement of a needle rotation drive.

The advantage of such variant is the possibility of a return output of a spiral needle from the sutured tissue. It reduces the sizes of the sewing device.

The second advantage is the absence of the sawing effect arising during stretching of a long string through sutured tissues.

The third advantage—there is no necessity in periodic taking out the thread from tissues after each coil or after several coils of atraumatic spiral needle.

However, there is a short disadvantage—a hollow spiral needle on diameter is bigger than an atraumatic spiral needle and can move only by a straight line

BRIEF DESCRIPTION OF THE DRAWINGS

In the further the invention is explained by the description of concrete variants of its realization and applied drawings, on which:

FIG. 11—a variant of the sewing device with the short spiral needle operated by one roller with a screw flute;

FIG. 12—clamping plates of the top and bottom gripping jaws with the handle of their moving;

FIG. 13—a cross-section on a line XIII-XIII on FIG. 11;

FIG. 17—a variant of the sewing device with the short spiral needle, operated by four rollers;

FIG. 18—a cross-section on a line XVIII-XVIII on FIG. 17 at the close position of tightening gripping jaws;

FIG. 19—cross-section on a line XIX-XIX on FIG. 17 at the close position of tightening gripping jaws;

DETAILED DESCRIPTION OF PREFERRED EMBODIMENTS

A Spiral Atraumatic Needle with Plural Spires

Figure 1:
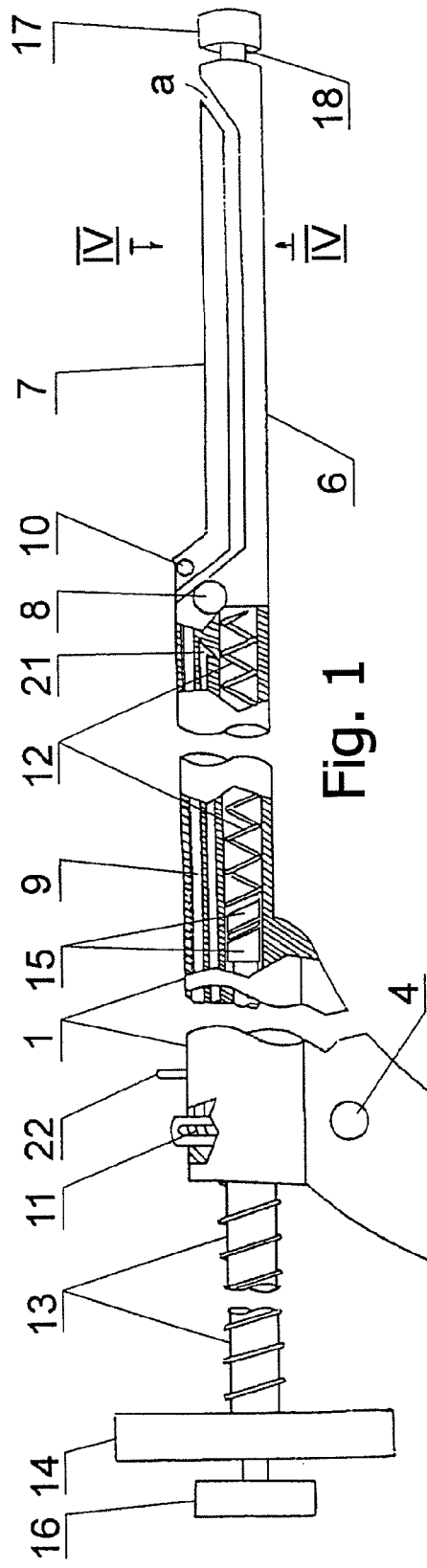
FIG. 1 represents the first variant of the sewing device with an atraumatic spiral needle with plural spires (a partial cut of the case), according to the invention.

FIG. 1 shows the first variant of the sewing device. The device contains the body 1 with the motionless handle 2. The mobile handle 3 is connected with motionless one by the central hinge 4. Both handles have rack mechanism 5 for fixing their mutual position.

Continuation of the body 1 in it distal part is the motionless tightening working gripping jaw 6. The mobile gripping jaw 7 is connected to a motionless gripping jaw 6 by a hinge 8. The mobile gripping jaw 7 is moving up and down with the help of a rod 9, which is connected to a mobile gripping jaw 7 by a hinge 10. In the proximal part the rod 9 is connected to the mobile handle 3 by a hinge 11. Thus, at movement of the mobile handle 3 mobile gripping jaw 7 goes up and down. Rack mechanism 5 rigidly fixes the position of the handle 3 and, hence, the position of the working gripping jaw 7. Other variants of management of position of a mobile working gripping jaw 7, for example, the screw mechanism of movement of a rod 9 that will allow to dose out more precisely efforts on compression of a stitched tissue, are possible also.

In this variant of the device realization, the spiral needle 12 contains such a quantity of coils, which is necessary for the length of a spiral to be equal or to exceed a little the length of the executed twining round stitches.

In the proximal part of the body 1 there is an internal screw thread on which the screw 13 with an external groove moves, but in some cases the screw 13 can be replaced with a core without a groove. On the proximal end of the screw 13 the handle 14 is located, and on its distal end the holder 15 of the tail part of a spiral needle 12 with pressed in it thread is established. This holder can be cone-shaped or have a screw thread on which the tail part of a spiral needle is wound.

The holder 15 also can contain two parts connected, for example, by the screw, located inside of the screw 13, and having the handle 16. At a turn of the handle 16 both parts of the holder 15 approach and clamp a tail part of a spiral needle 12. At a turn of the handle 16 in an opposite side the spiral needle 12 is released. Other variants of performance of the holder 15 are possible also.

Means for capture of the sharp end of a needle and-or a string on the end of the stitched seam, in this case a jack 17, is established on the distal end of a motionless gripping jaws 6 on an axis 18 having on the end a screw cutting. It allows to the jack 17 to rotate and be disconnected from a gripping jaws.

Figure 2:
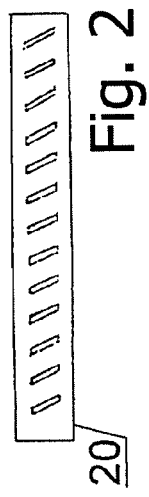
FIG. 2—a clamping plate of a mobile gripping jaw with openings for a spiral needle.
Figure 3:
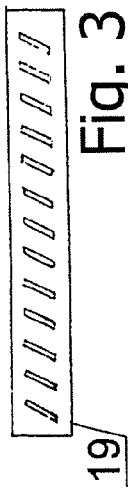
FIG. 3—a clamping plate of a motionless gripping jaw with openings for a spiral needle.
Figure 4:
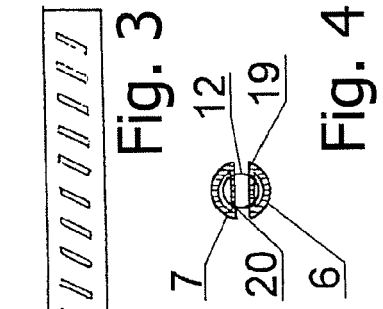
FIG. 4—a cross-section on a line IV-IV on FIG. 1.

The spiral needle 12, which tail part is clamped in the holder 15, in a starting position settles down before tightening working gripping jaws 6 and 7. At rotation of the handle 14 screw 13 is screwed in the body 1 and rotates a spiral needle 12. The needle 12, rotating, is entered into a cavity of the shown gripping jaws 6 and 7 and stitches on a spiral the tissue fixed in them. Clamping plates 19 and 20 (FIG. 2 and FIG. 3) with directing opening not only supervise a direction of movement of a spiral needle 12 at its rotation, but also provide completeness and reliability of sewing tissues together. It is reached by that the spiral needle; in openings of the plates 19 and 20 rises above a surface of the tissue compressed by clamping plates (FIG. 4).

After tissue sewing for all demanded length of a suture, the needle 12 leaves in the distal end of a motionless gripping jaws 6 and gets with the sharp end in a jack 17 where it is solidly fixed. After return turn of the handle 16 tail end of a needle is released, as it has been described above. At rotation of a jack 17 the needle 12 is completely taken out from the tissue. Thus, during a suture, periodically, after each coil or after 2-3 coils the string, stitching tissues fixed by a clip, is grasped by a hook 21 for capture of a string and extended from tissues at moving the handle 22 of the hook 21 for capture of a string. Frequency of the hook 21 use for taking out the thread depends on density of a stitched tissue and character of a used thread (how much its external surface is polished).

After between gripping jaws 6 and 7 tissue is stitched by a twining round stitches, the working gripping jaw 7 rises, releasing the stitched tissue. The device for sewing is taking out. The distal end of the stitched string is stretched and fixed by one of listed above ways.

Figure 5:
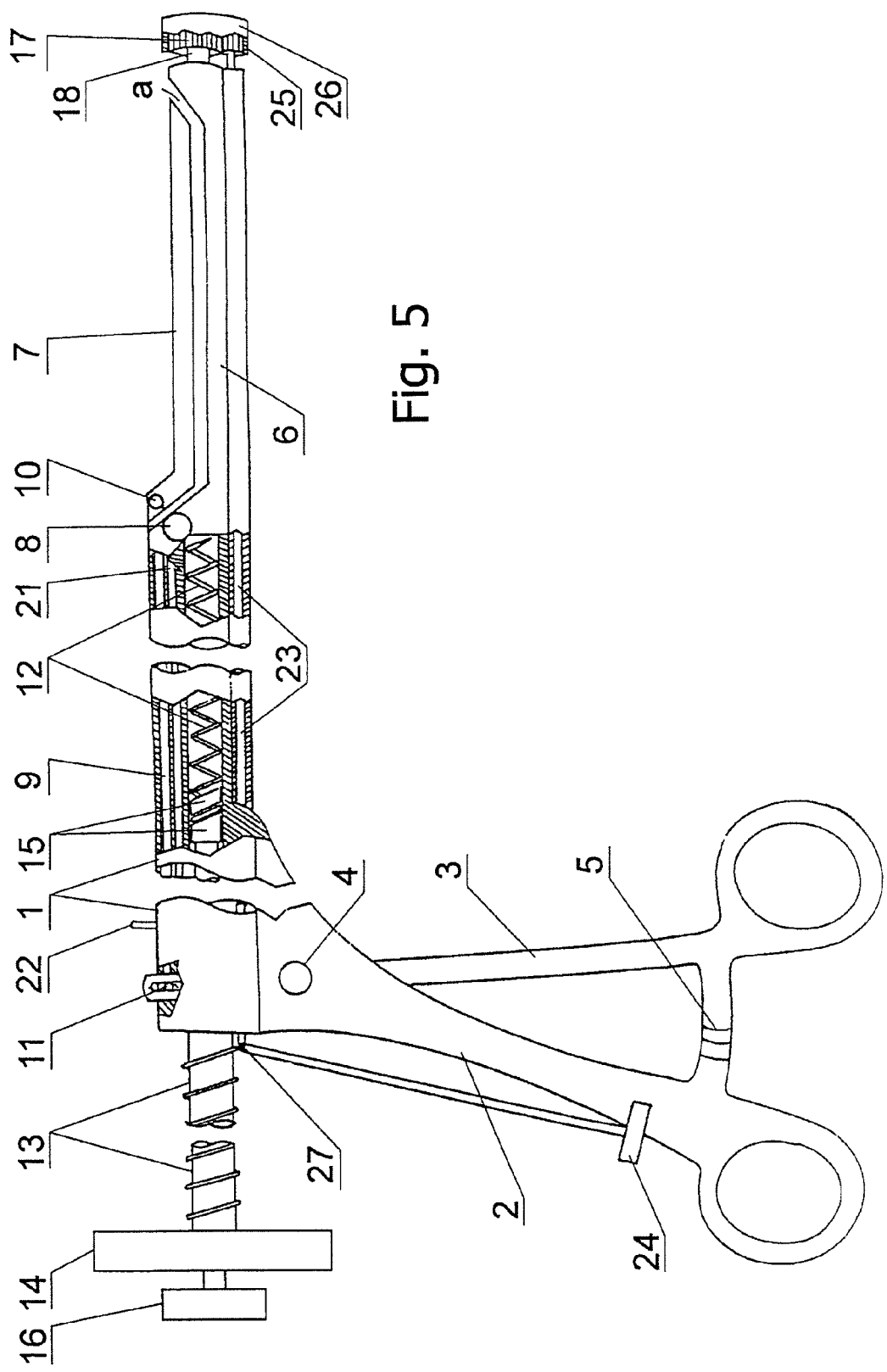
FIG. 5—a variant of the sewing device with an atraumatic spiral needle with plural spires, with in parallel located mechanism of remote removal of a needle from the stitched tissues (a partial cut of the body)

In the given variant for taking out the spiral needle 12 from the stitched tissues a jack 17 is rotated manually. It is not always convenient. FIG. 5 shows the variant of performance of the device, adapted for remote rotation of a jack 17 is shown. For this purpose the shaft 23 with the handle 24 on its proximal end and the cylinder 25 on the distal end is stipulated. The cylinder 25 adjoins its surface to an external lateral surface of a jack 17 and has on its external surface a cogwheel, which enters into gearing with a corresponding cogwheel on the external surface of a jack 17. Gear gearing is protected by a casing 26. The shaft 23 of a jack 17 rotation is done folding in the hinge 27, but it is possible to execute an external part of a shaft 23 in the form of a flexible shaft. After the termination of work by the handle 14 and her installation in horizontal position, a shaft 23 is straightened, the rotation of the handle 24 results in rotation of a jack 17 and taking out the spiral needle 12, clamped by the sharp end in a jack 17, from the stitched tissues.

Figure 6:
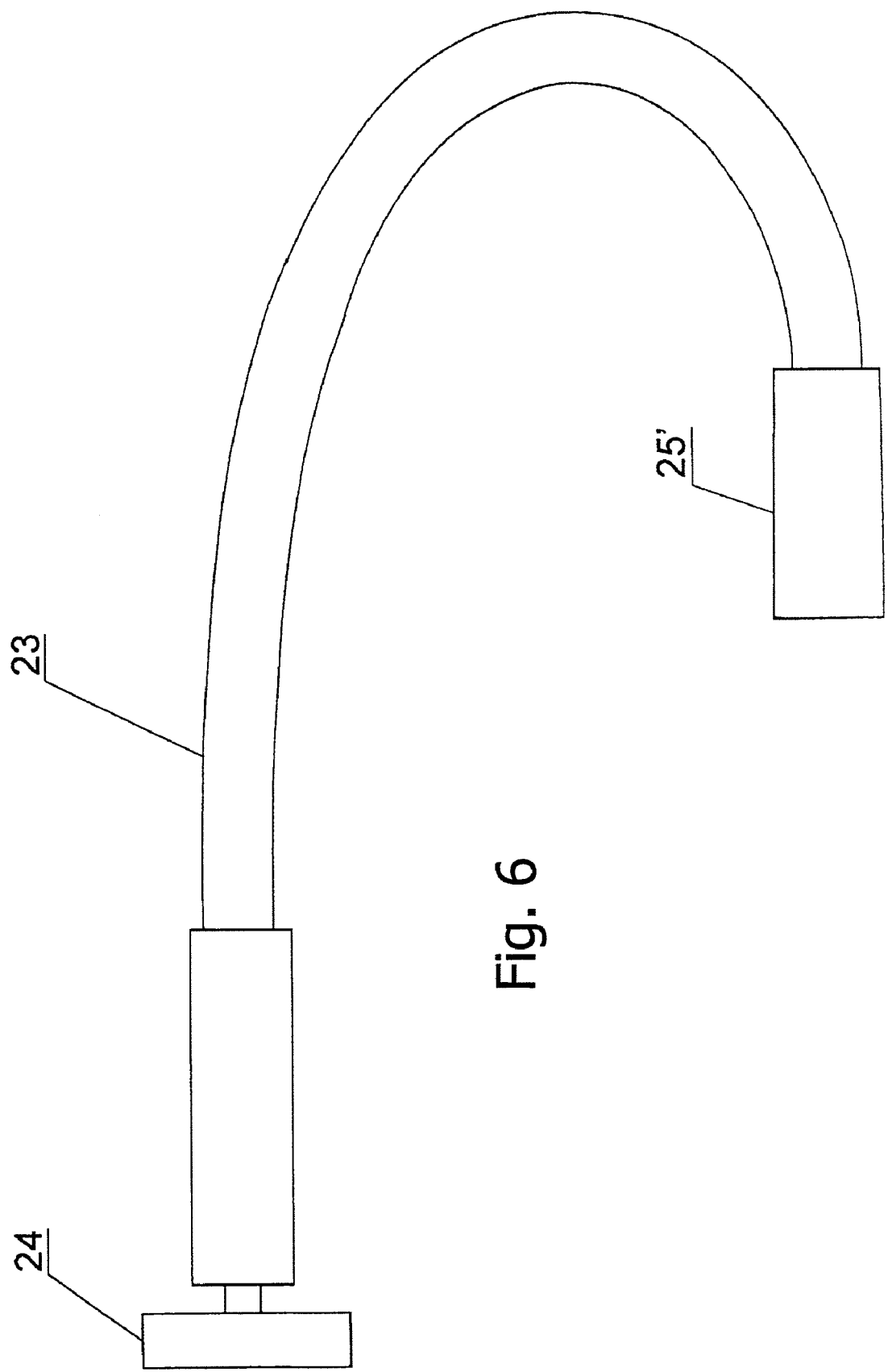
FIG. 6—a demountable flexible shaft for rotation of a spiral needle with plural spires.
Figure 7:
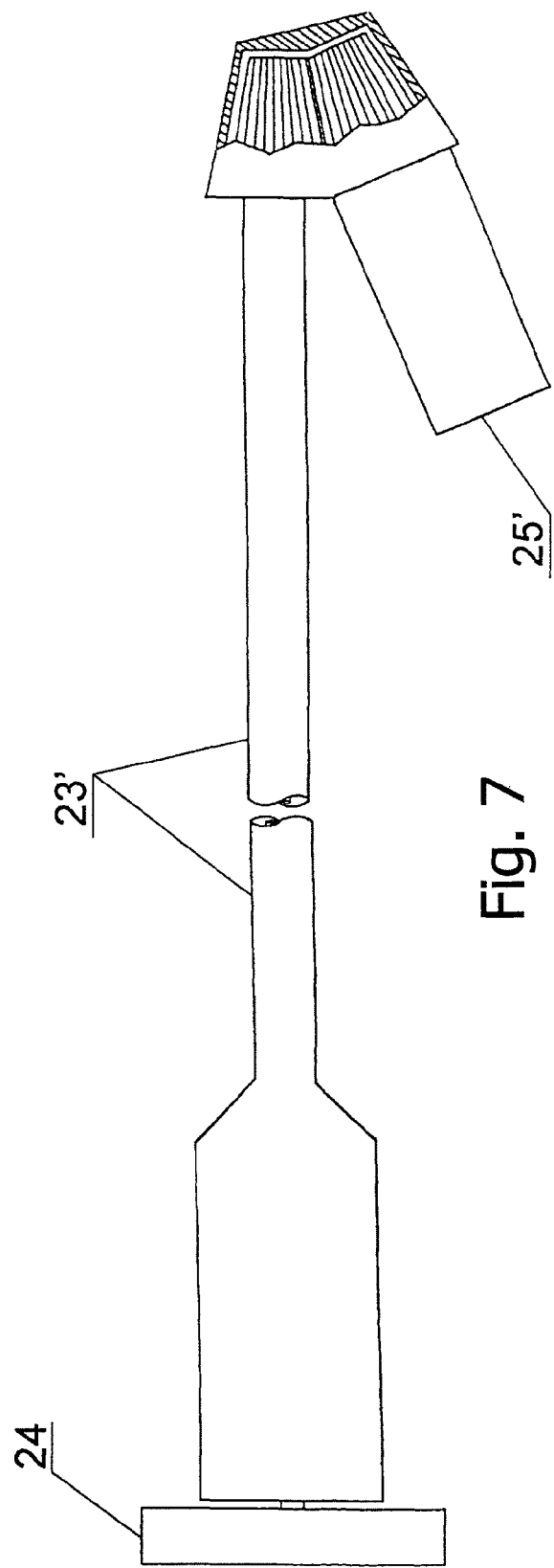
FIG. 7—a demountable gear drive for rotation of a spiral needle.

Other variant of rotation of the jack 17, shown on FIG. 6 and FIG. 7, is possible also. FIG. 6 shows the flexible shaft 23, which on one end has the handle 24 for rotation of a jack, and on other—the cylinder 25' which is hafted on a jack 17, is shown. At rotation of the handle 24 flexible shaft 23 through the cylinder 25' rotates a jack 17. It leads to a withdrawal of a spiral needle 12 from the stitched tissues.

Referring to FIG. 7, instead of a flexible shaft (which sterilization presents certain difficulties) the shaft 23, where the cylinder 25' is connected with the rotations handle 24 by a conic tooth gearing is presented. Instead of the specified conic tooth gearing systems of the cardan joint or other devices with an adjustable corner of the turn, described in RU 2284160 can be used. In this variant also the cylinder 25' is hafted on a jack 17 and rotation of the handle 24 leads to rotation of a jack 17.

These devices for the rotation, shown on FIG. 6 and FIG. 4, can be used (with certain modifications) and for rotation of the tail parts of a needle 12 of a holder 15, i.e. for sewing of the tissues.

FIG. 5 shows other variant of a mechanical drive for rotation of a spiral needle 12. In this variant the spiral needle 12 settles down inside of the rotating cylinder 28 having an internal screw thread which step precisely corresponds to distance between coils of a spiral needle 12. The internal screw thread in the cylinder 28 can be on all its internal surface (for sewing together the dense tissues), but in cases of sewing together the soft tissues there is enough groove only in a distal department of the cylinder 28 for interaction with several coils of a spiral needle 12.

The forward, sharp end of a spiral needle 12 is prominent from this cylinder and settles down in directing opening in a distal department of the device body 1 before working gripping jaws 6 and 7. The cylinder 28 is rotated by the handle 14, fixed on the proximal end of the cylinder 28. It is possible to replace the handle 14 with one of the rotation devices, shown on FIG. 6 or FIG. 7.

At rotation the cylinder 28 transfers rotary movement to a spiral needle 12, located inside, which sharp end is located in directing grooves outside of the cylinder 28. The spiral needle 12 on directing openings is directed into an internal cavity of working gripping jaws 6 and 7 and stitches the tissue fixed in gripping jaws. Then the needle 12 gets by the sharp end in a jack 17 and is taking out from tissues by one of described above ways. In this variant disappears necessity for the tail part spiral needle holder 15.

Figure 8:
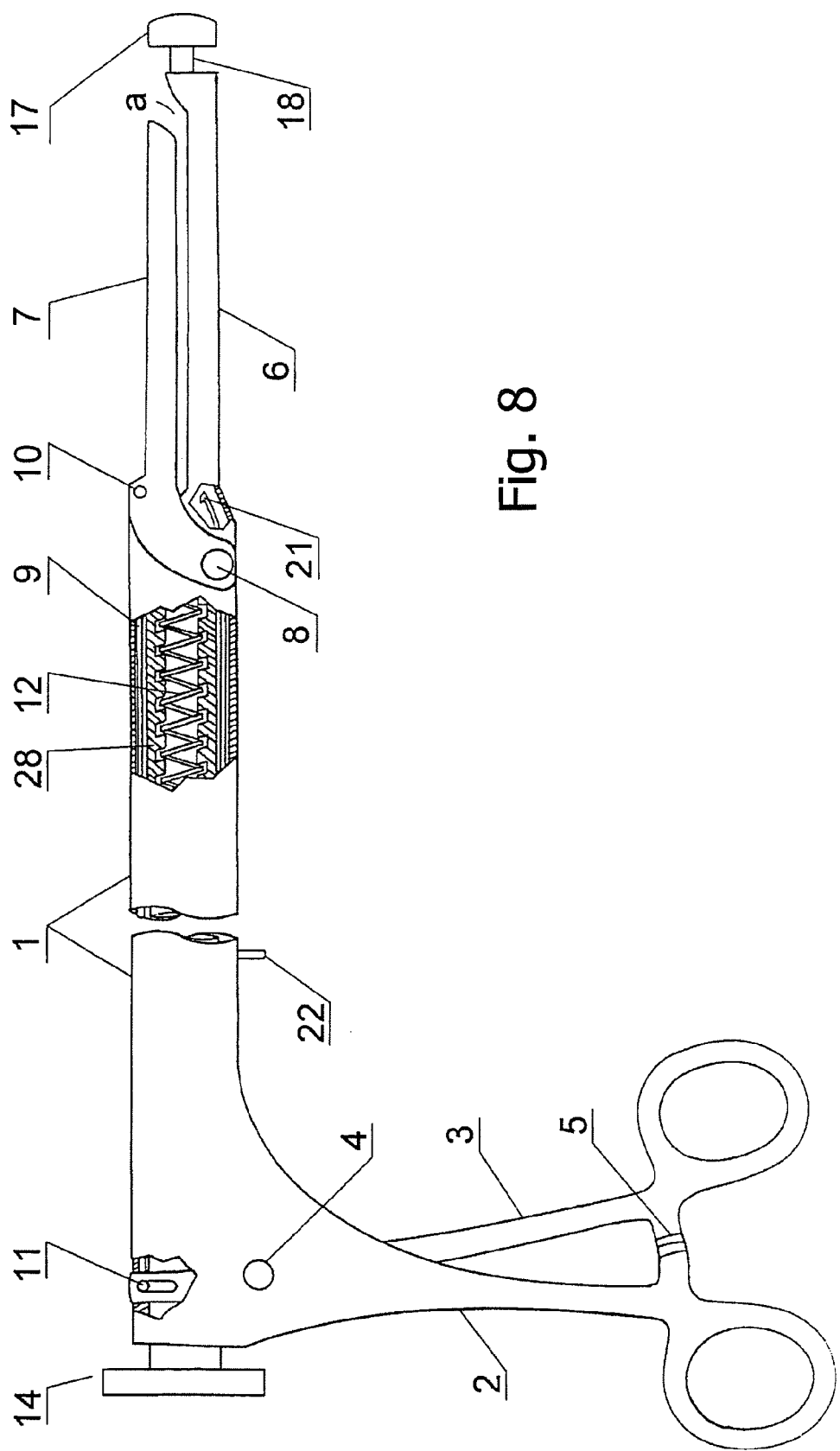
FIG. 8—a variant of the sewing device with the cylinder with an internal screw thread.

Variants of the device in which the spiral needle leaves tissues, not changing a rectilinear direction of movement, are shown on FIGS. 1, 5 and 8. It is possible in two cases: 1) all stitched tissue keeps within gripping jaws of a clip; 2) the stitched tissue is wider than length of gripping jaws, but not stitched part of the tissue is soft enough and can be taken out in the distal end of a mobile gripping jaw 7 under some angle to it.

For this case the special interval between the distal end of a mobile gripping jaw 7 and a jack 17 for capture of the sharp end of a needle on a motionless gripping jaw 6 is provided (see FIGS. 1, 5 and 8).

Figure 9:
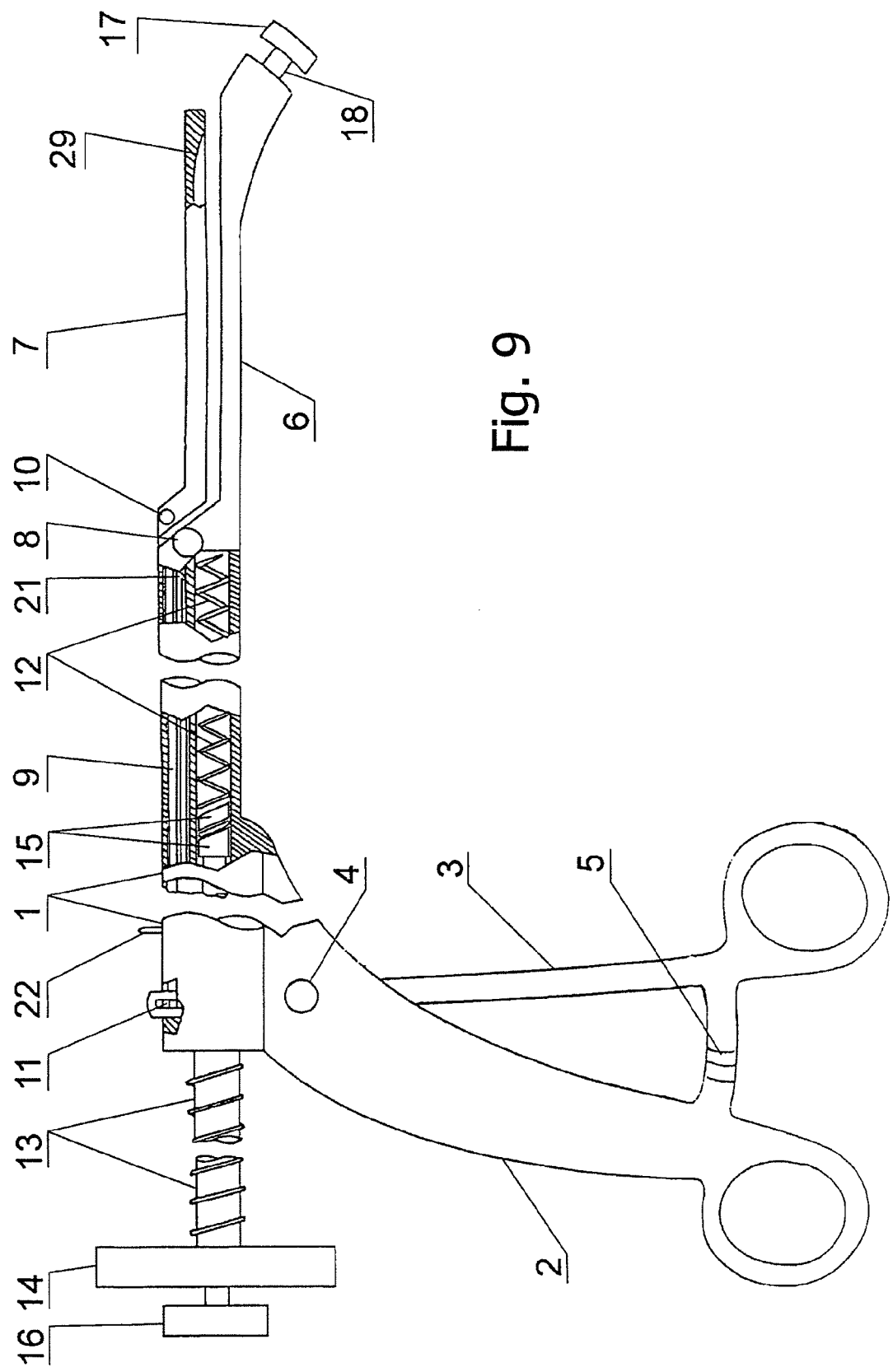
FIG. 9—a variant of the sewing device with a mechanism for a spiral needle withdrawal under an angle to a line of tissues sewing.

FIG. 9 shows other variant of gripping jaws in cases when the tissue cannot be placed in this interval. In this variant the distal end of a motionless gripping jaw 6 is bending under some flat corner. On an internal surface of the distal end of a mobile gripping jaw 7 there is a directing slant 29, which slightly rejects the sharp end of a spiral needle 12.

The spiral needle 12 at the progress movement deviates from a direct direction and gets in a curved part of a motionless gripping jaw 6, on which end the jack 17 for the sharp end of a needle 12 is settled down. The needle 12 is unscrewed from tissues under the specified angle. This variant is possible at sufficient flexibility of a spiral needle.

Figure 10:
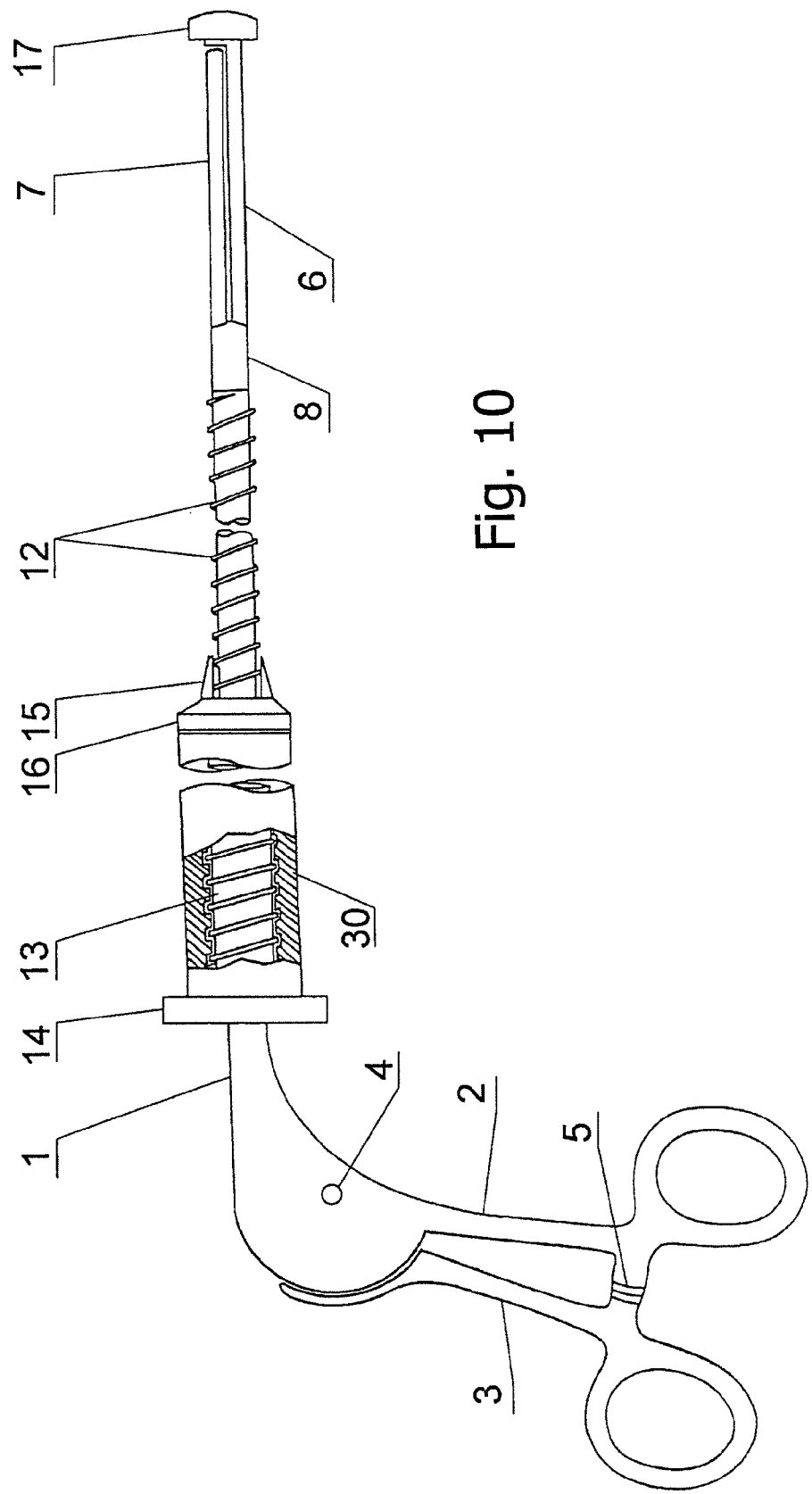
FIG. 10—a variant of the sewing device with an external arrangement of a spiral needle with plural spires.
Figures 14, 15:
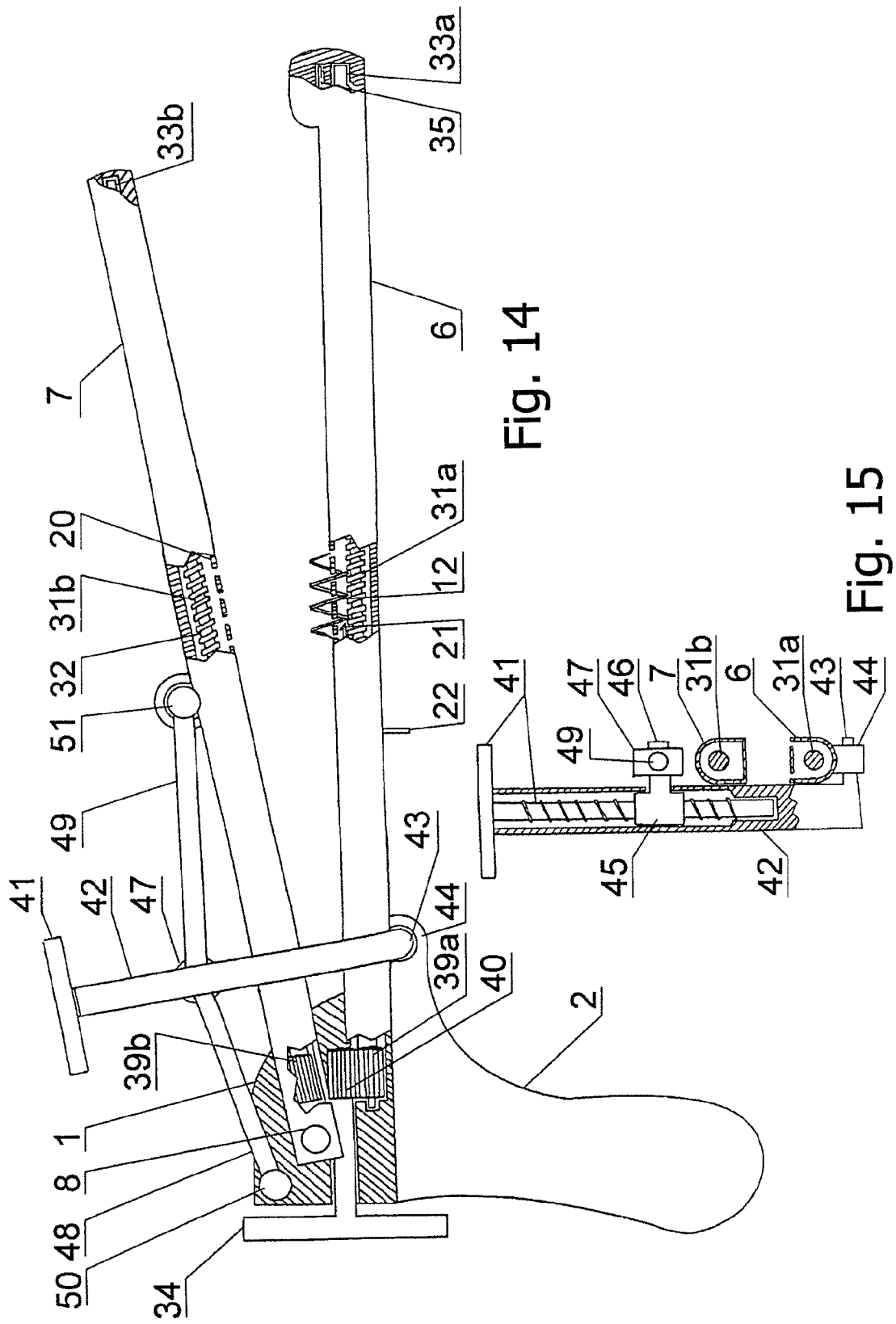
FIG. 14—a variant of the sewing device with the short spiral needle, operated by two rollers with a screw flute.
FIG. 15—the operating screw, side view, partial cut.

FIG. 10 shows the variant of the sewing device according to the invention, with an external arrangement of a long spiral needle with plural spires. For this variant can be used a standard long endoscopical clip, for example 5 mm in diameter. In this case in a proximal part of the body 1 of a sewing device, the screw 13, on which the cylinder 30 with a corresponding internal screw thread rotates, is settled down. In some cases instead of the cylinder 30 the hollow cylinder without a screw thread can be used, since the sewing step at rotation around of rigid directing is defined by a design of a spiral needle 12. In a proximal part of the cylinder 30 the handle 14 for its rotation settles down. In a distal part of the cylinder 30 there is a holder 15 for the fixation of the tail end of a spiral needle 12. On the given figure the variant of a collet clamping device for the fixation of a spiral needle is shown. The handle 16 at rotation in one direction leads to the fixation of a tail part of a spiral needle 12 in a collet clamp, at rotation in other direction—the needle 12 is released.

In the device body 1 and in one of its working gripping jaws the longitudinal groove, in which settles down a hook 21 for capture of a string and its handle 22, is provided.

Then the tissue to be sewed is clipped by working gripping jaws 6 and 7 and the correctness of clip imposing is checked, the handle 14 is rotated. The spiral needle 12 stitches tissues, and then is taken out from tissues, as well as in the previous variants. For this purpose on the distal end of one of gripping jaws the jack 17 for capture of the sharp end of a spiral needle is located. Jack 17 together with the stitched needle 12 is rotated manually or by means of shown on FIG. 6 or FIG. 7 rotating devices. The needle 12 is taken out from tissues. A string following a needle is periodically drawn out by a hook 21 for capture of a string. Then gripping jaws 6 and 7 are slightly opened and taken out from under the stitched string, the twining round string is tightened.

This variant can be used also if it is necessary to do the second suture after the first stitching on internal directing, as it has been described above.

Short Spiral Atraumatic Needle

Variants of sewing devices with the short spiral needle comprising two, three or four coils are presented on FIGS. 11-17.

FIG. 11 shows the variant in which the short spiral needle 12 comprising 3-4 coils is used. This needle is moved by rotation of one roller 31.

In a motionless gripping jaw 6 to a spiral needle 12 is tightly adjoined a roller 31, which has a screw flute 32 which step is equal in a described variant to a step between coils of a spiral needle 12. The distal end of a roller 31 rotates in the bearing 33 established in the distal end of a motionless gripping jaw 6. On the proximal end of a roller 31 there is a handle 34 for its rotation. The roller 31 at its rotation has no translational movement, the position of a screw flute 32, with which coils of a spiral needle 12 cooperate, changes only.

On the sides of gripping jaws 6 and 7, turned to each other, demountable clamping plates 19 and 20 are located. They take the central part of a zone of a clip in working gripping jaws, leaving on each side a narrow crack for pass of a spiral needle 12 and a string following it (see FIG. 13—a cross-section of working gripping jaws on a line XIII-XIII). In a motionless gripping jaw 6 clamping plate 19 in a distal part is inserted into a groove 35 in the body of a gripping jaw, and in a proximal part it is fastened to the handle 36.

In a mobile gripping jaw 7 clamping plate 20 in a distal part also is inserted into a similar groove in the body of this gripping jaw, and in a proximal part is connected to the handle 36 by means of the hinge 37 (FIG. 12). It enables a mobile gripping jaw 7 to be open and to be closed freely.

The surface of clamping plates 19 and 20, adjoining to stitched tissues, can be covered by a thin biocompatible grid or a film as it is specified earlier.

The spiral needle 12 in a starting position (FIG. 12) is about the ends of clamping plates 19, 20 in their proximal part near the handle 36. Then the working gripping jaws 6 and 7 are brought together, the spiral needle 12 can rotate and move around of clamping plates 19 and 20 which in this case are directing for it. Rotation of a roller 31 forces the spiral needle 12, pressed to a clamping plate 19 (FIG. 13), also to rotate on a spiral, stitching tissue fixed between gripping jaws 6 and 7.

Periodically, during the suture, the string following a needle, is grasped by a hook 21 and is extended from stitched tissues by means of the handle 22 of hook 21. It is possible to do it after each coil of a needle 12, but at presence of a string with the polished surface which facilitates sliding of a string in tissues, it is possible to extend a string through 2-3 or more coils. After suture of the tissues placed between gripping jaws 6 and 7, the spiral needle 12 sharp end gets in a jack 17 and is fixed in it.

After those gripping jaws 6 and 7 are slightly brought apart and clamping plates 19 and 20 are taken out from gripping jaws moving the handle 36 in a proximal direction lengthways opening 38, available in the body 1. The grid or a film covering an internal surface of clamping plates 19 and 20 remains on the surface of the stitched tissue, facilitating removal of clamping plates. Then, completely having opened gripping jaws 6 and 7, the suture device is taken out, the ends of the twinning round seam are tightened and fixed, as is specified earlier.

Considering, that the main thing in work of the given variant of the sewing device is dense connection of a roller 31 with a screw flute 32 to directing plate 19, between which the spiral needle 12 settles down, the form of a directing plate 20 in a mobile gripping jaw 7 can be another, for example, with openings, as well as in the previous variants. At this form the clamping plate 20 will not interfere with opening of working gripping jaws after suture and have not to be taken away. It simplifies the design.

On FIG. 9 the variant with two rollers 31a and 31b, on which surface the screw flute 32 is done, is shown. Rollers draw in a spiral needle 12 from two sides. This variant can be used for suture of more dense tissues. For this variant it is better to use the body with two long gripping jaws 6 and 7, connected by an axis 8 located in a proximal part of the body 1. It enables to bring apart the distal ends of gripping jaws 6, 7 as much as possible, and, at the same time, the proximal ends are taken apart minimally.

Therefore the design of a rotating roller 31b in a mobile gripping jaw becomes simpler—it is similar to a roller 31a in a motionless gripping jaw. Rollers 31a and 31b in distal parts rotate accordingly in hinges 33a and 33b. Rollers 31a and 31b have cogwheels 39a and 39b in a proximal part. In a proximal butt-end of the body 1 the handle 34 for rotation of rollers 31a and 31b is placed. On the end of the handle 34 there is a cogwheel 40. The cogwheel 40 is placed between cogwheels 39a and 39b and is in gearing with them at the closed gripping jaws 6 and 7. At the open gripping jaws the cogwheel 39b leaves gearing with a cogwheel 40, but at pressure of the working gripping jaws 6 and 7 gearing between these cogwheels is restored. Therefore at the closed gripping jaws 6 and 7 rotation of the handle 34 leads to rotation of rollers 31a and 31b, and they rotate in one direction. Rotation of rollers 31a and 31b forces to rotate the spiral needle 12, clamped between them, which at the rotating translational movement is screwed in a stitched tissue.

The mechanism of compression and opening of a similar design of gripping jaws can be various. The simplex variant can be the screw compressing working gripping jaws. However, an arrangement of the screw in proximal parts of working gripping jaws is expediently only then the working gripping jaws are short enough.

In designs with long working gripping jaws it is better to use a variant of the screw for compression and opening of working gripping jaws 6 and 7 with system of levers. This variant is presented on FIGS. 14 and 15.

The screw 41 is located inside of the body 42 having three entire walls and one open or partially open wall. On the bottom end of the body 42 there is an emphasis 43 inserted, with a possibility of rocking, in a ring 44, fixed on a motionless gripping jaw 6 or in the handle 2 of device body 1. On the screw 41 at its rotation the toddler 45, having an internal screw thread, corresponding to a screw thread of the screw 41, moves. In a lateral wall of a toddler there is a probe 46 which is inserted into the central hinge 47 of levers 48 and 49.

The proximal lever 48 is attached to the device body 1 by means of the hinge 50, and the distal lever 49 is attached to a mobile gripping jaw 7 by means of the hinge 51. Both of the levers are connected together by means of the central hinge 47. An axis of the central hinge 47 is the probe 46 inserted into it. Thus, the effort from the screw 41 through the probe 46 and the central hinge 47 is distributed on levers 48 and 49.

Created distribution of forces is such, that the final point of application of force from the screw 41 settles down near to the center of a mobile gripping jaw 7 at a proximal placement of the screw 41.

Figure 16:
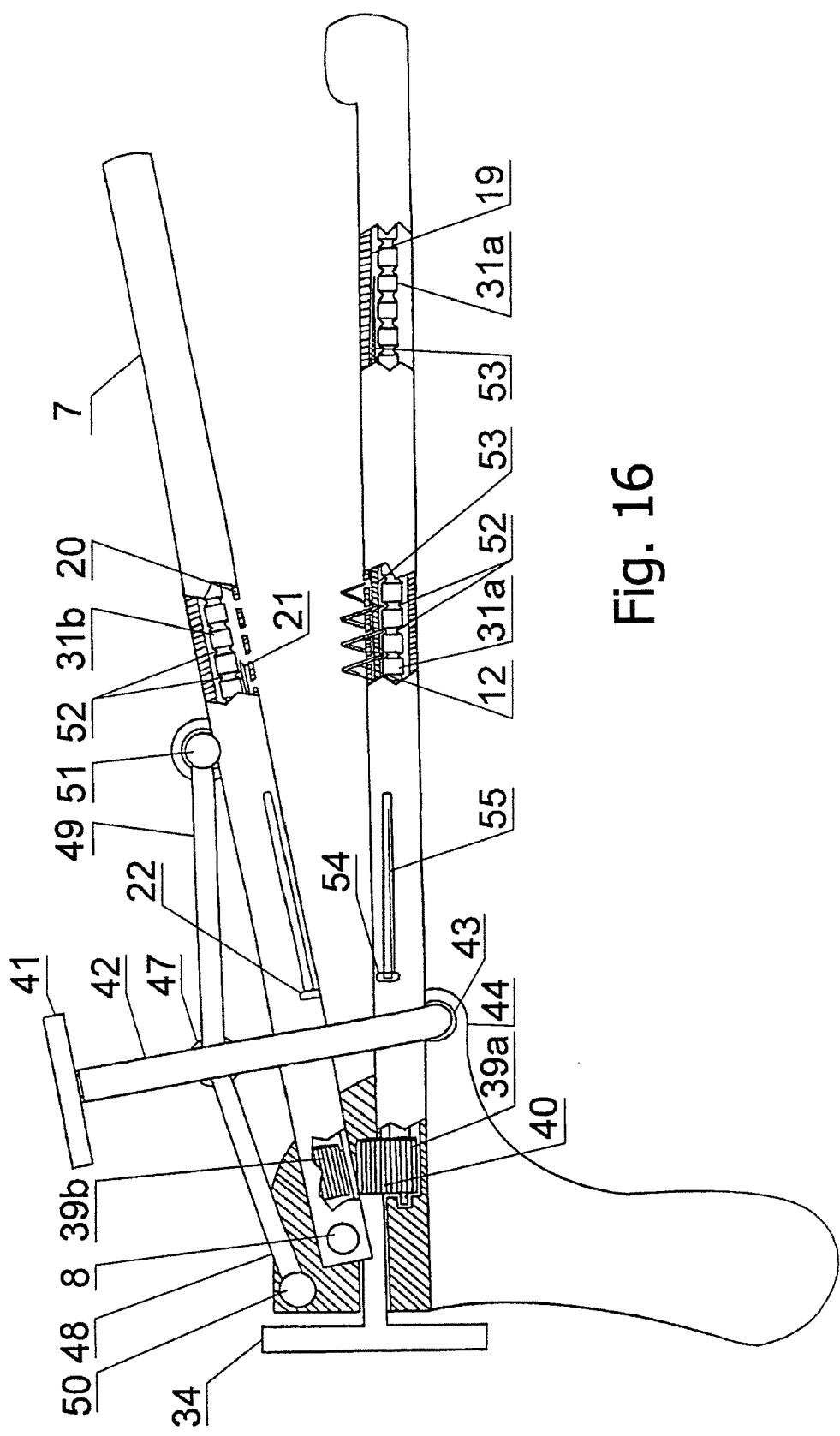
FIG. 16—a variant of the sewing device with the short spiral needle, operated by two rollers with set of parallel cylindrical flutes on a surface.

FIG. 16 shows the variant of the device which works similarly to the described above. However, unlike the previous variant, here are used rollers 31a and 31b, on which surface the set of the parallel cylindrical flutes 52, placed on distance equal to distance between coils of a spiral needle 12, is executed. Besides this variant of the device is more universal and is suitable for sewing together both thicker, and thinner tissues.

For this purpose one of clamping plates, in this case a plate 19, is established with a possibility of moving in a direction, perpendicular to the plane of a clip, and has the variable thickness increasing to the distal end. Under a plate 19 the wedge-shaped sealant 53, increasing on thickness in a direction from the distal end to the proximal end, settles down.

This sealant 53 is established with a possibility of recurrent-translational movement along a clamping plate 19. On the proximal end of a sealant 53 there is a handle 54. At moving the handle 54 on directing groove 55 the sealant 53 moves, providing necessary displacement of a clamping plate 19 in relation to a motionless plate 20 at sewing together more thin tissues.

It is also possible to establish a clamping plate 19 on springs of corresponding rigidity.

One more variant with the short spiral needle 12 comprising 2, 3 or 4 coils is presented on FIGS. 17, 18 and 19. In this variant the spiral needle 12 is drawn in from four parties by smooth rollers 56a, 56b, 56c and 56d as it is shown on a cross-section on a line XIX-XIX (FIG. 19). In this case also it is better to use a variant of the device with the long working gripping jaws fastened by an axis 8, located in a proximal department of the device.

In this variant rollers 56c and 56d in a mobile working gripping jaw 7 are similar to rollers 56a and 56b in a motionless gripping jaw 6 and do not change their position at any position of a mobile working gripping jaw 7. On the proximal ends of rollers are placed accordingly cogwheels 39a, 39b, 39c and 39d, entering in gearing with a cogwheel 40 which is on one axis with the handle 34 of the screws (FIG. 18—a cross-section by a line XVIII-XVIII).

Cogwheels of rollers 56a and 56b, located in a motionless gripping jaw 6, constantly are in gearing with a cogwheel 40. Cogwheels of rollers 56c and 56d, placed in a mobile gripping jaw 7, at opening of the mobile gripping jaw 7, leave gearing with a cogwheel 40; however at closing of a gripping jaw 7 again enter into corresponding gearing. Therefore at the closed gripping jaws 6 and 7 at rotation of the handle 34 all rollers of mobile and motionless gripping jaws are rotating in one direction.

The short spiral needle 12, drawn in from four parties, rotates and stitches fixed between gripping jaws 6 and 7 tissues. For increase the surface of coupling of rollers 56a-56d with a spiral needle 12 on rollers can be provided notches of the various form or circular flutes into which the small sector of a spiral needle enters. In this case coupling of rollers 56a-56d with a spiral needle 12 occurs not only on an external surface of a needle, but also on its lateral surfaces.

According to this variant clamping plates 19 and 20 with openings, as shown on FIG. 1, which do not need to be taken out after suture are used.

Also, as well as in all previous variants, the mechanism of strings drawing out of stitched tissues after each coil of a spiral or after several coils by a hook 21 by means of the handle 22 is provided.

The mechanism of management of disclosing and closing of gripping jaws 6 and 7 has no basic importance. Except for the screw mechanism shown on FIGS. 9 and 10, one of the possible variants is presented on FIG. 11 where the mobile handle 3 has an axis 4 located in a distal department of the body 1 before motionless gripping jaw 6. By pressing the handle 3 it influence the middle of a mobile gripping jaw 7 with its fulcrum point.

Rack mechanism 5, fixing handle 3 position, is located on the end of the handle 3 and in a proximal department of the body 1. Working gripping jaws 6 and 7 are moved apart by a flat spring 57.

Advantage of these variants is the opportunity to use a short spiral needle which after suture is completely located in a jack 17. It allows creating more compact stitching device.

Variants of fastening of the stitching device on a usual clip are possible (FIGS. 20-23). For this purpose on each clip gripping jaw fastens one working gripping jaw of the stitching device. In these variants both working gripping jaws 6 and 7 can be settled down perpendicularly or under other angle to handles. At perpendicular or coming nearer a perpendicular arrangement to handles working gripping jaws settle down in parallel or nearly in parallel to each other, that creates the best conditions for suture.

Figure 20:
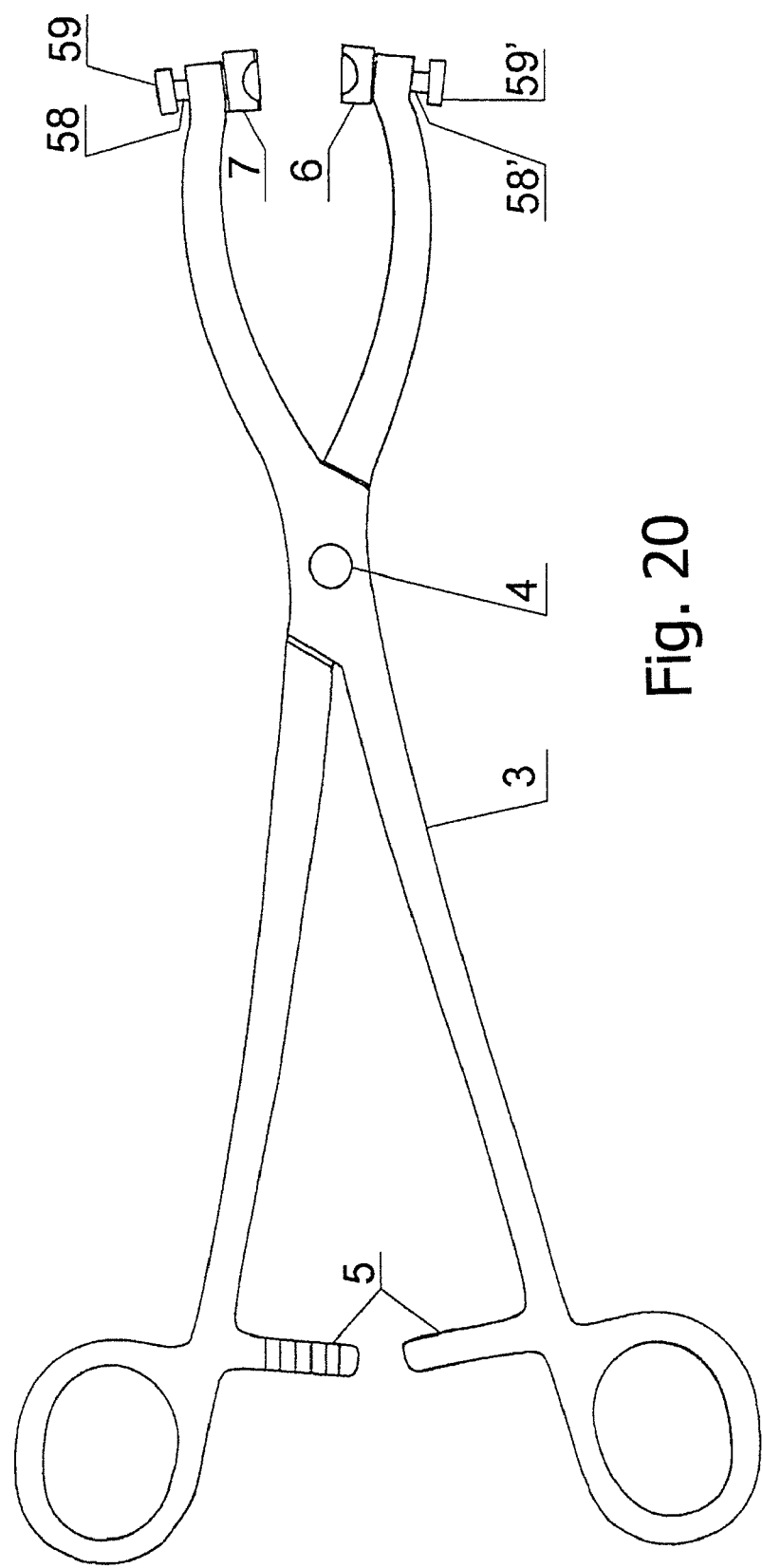
FIG. 20—a variant of the sewing device with the tightening working gripping jaws established on a clip under an adjustable angle.
Figure 21:
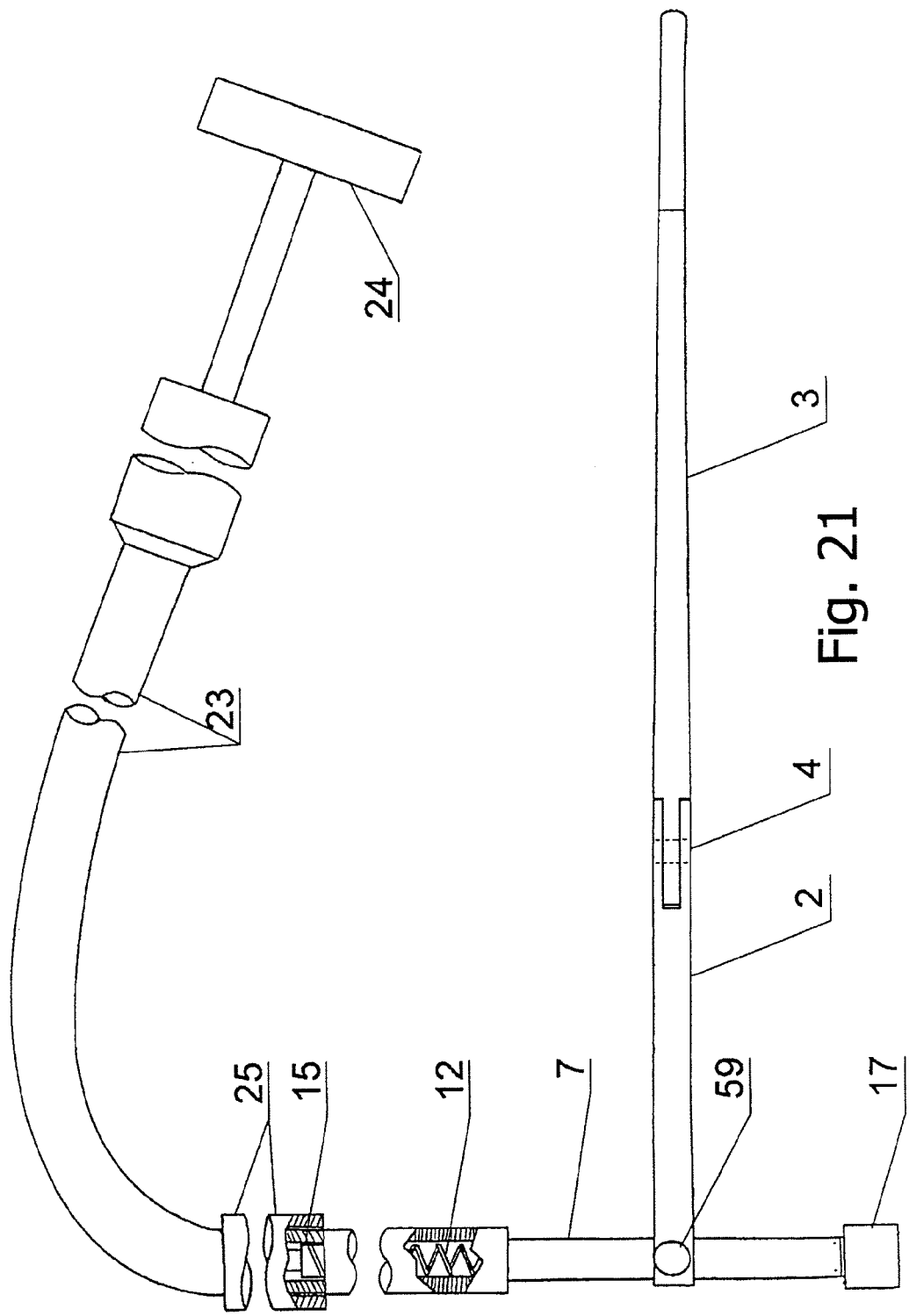
FIG. 21—a variant of the sewing device with the tightening working gripping jaws established on a clip with an adjustable angle, with the connected demountable flexible shaft.
Figure 22:
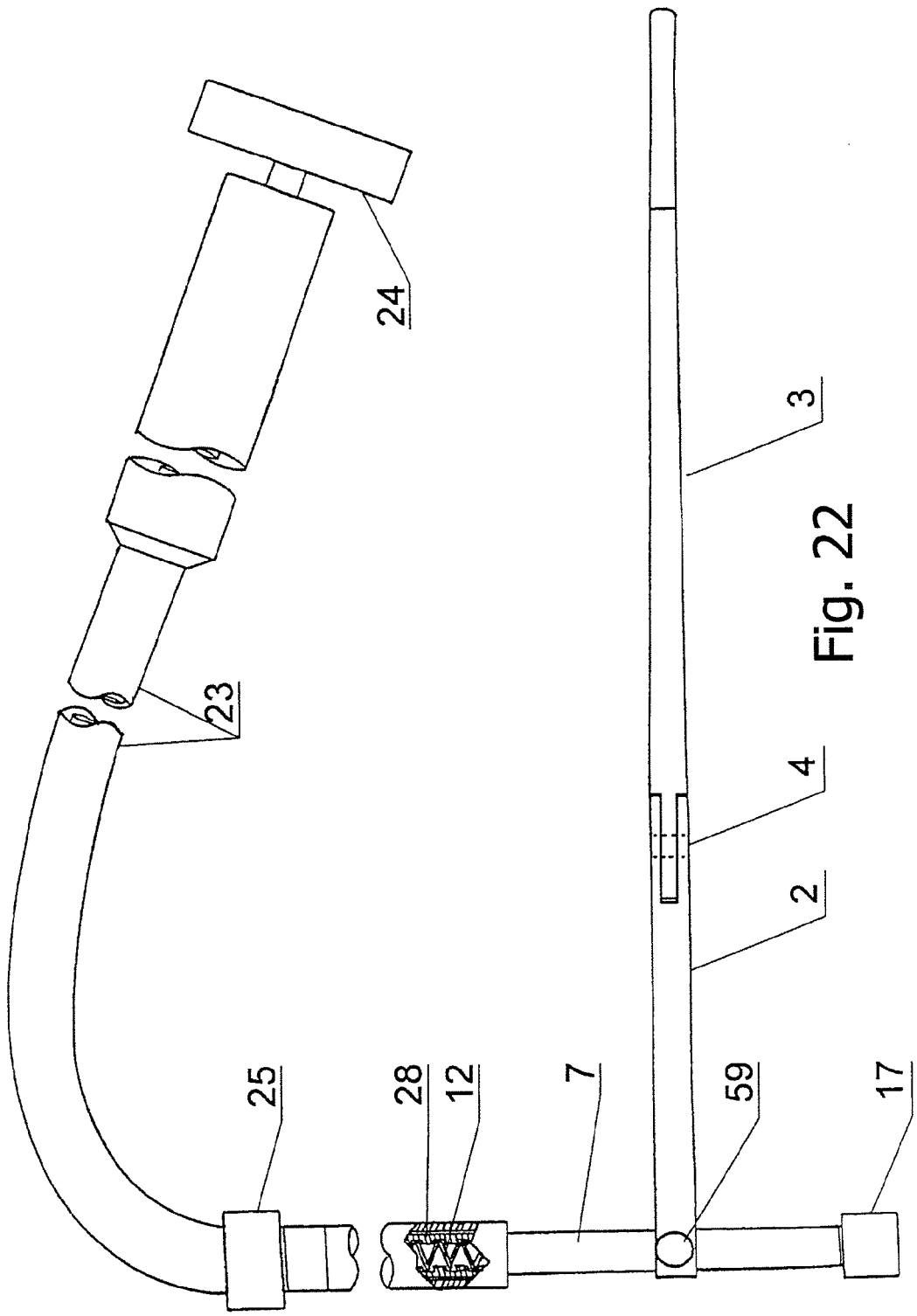
FIG. 22—the same device, as on FIG. 21, but with a needle located in the cylinder with an internal thread.
Figure 23:
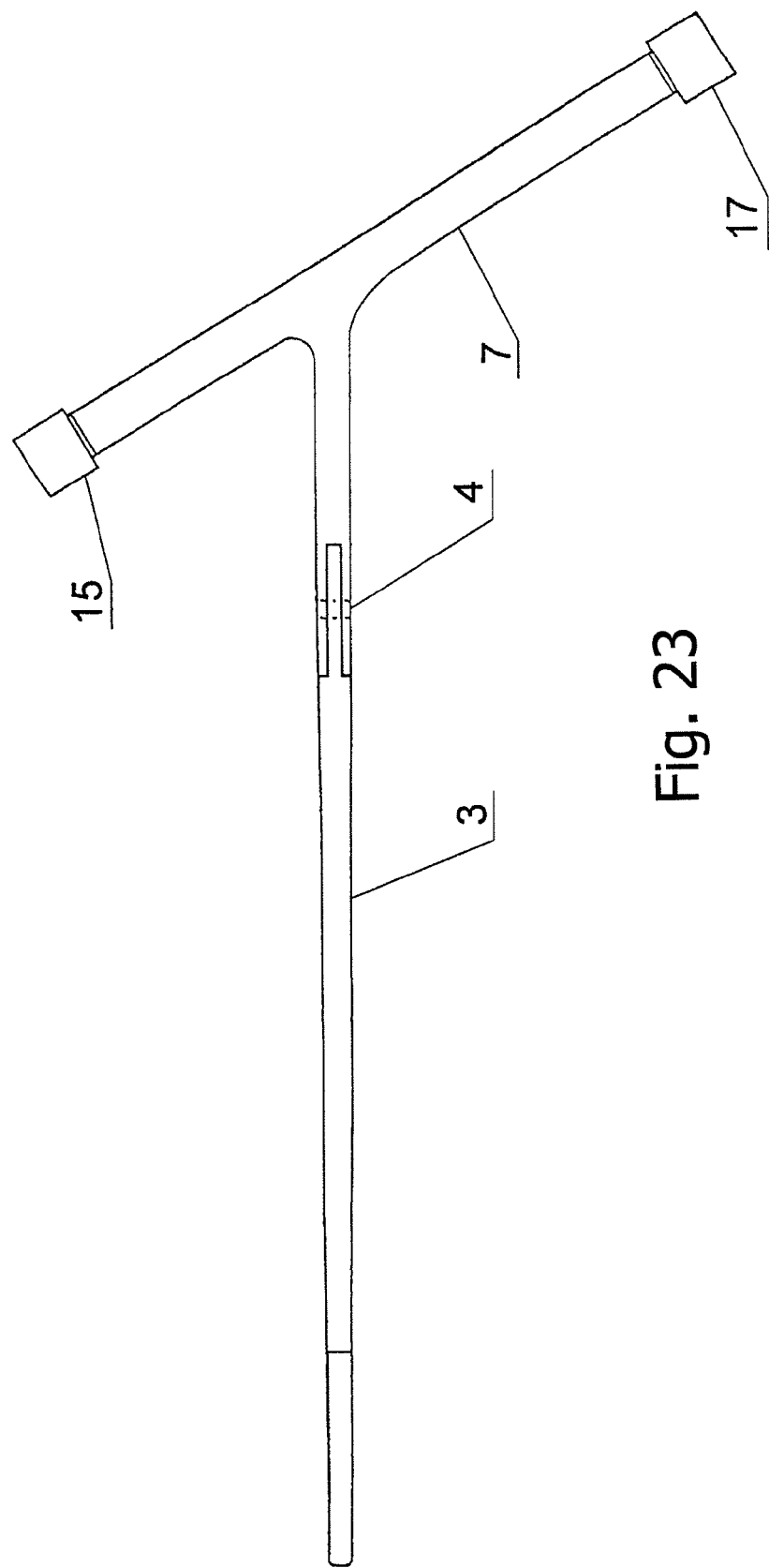
FIG. 23—a variant of the sewing device with the tightening working gripping jaws rigidly fixed on a clip under a constant angle.

The angle of the arrangement of working gripping jaws in relation to handles can be rigidly fixed (FIG. 23), but can be adjustable (FIGS. 20-22). In this case (FIG. 20) each working gripping jaws incorporates to the body of a clip with an axis 58 and 58' accordingly, which is fixed by the screw 59 and 59'. Having connected working gripping jaws together in position of the closed clip, an angle necessary for work is established between handles of a clip and working gripping jaws. In this position twist screws 59 and 59', strongly fixing the chosen corner. In this position screws 59 and 59' are twisted, strongly fixing the chosen angle. In the further work of these variants of the sewing device is similar to the work described above.

As shown in FIGS. 21 and 22, on the one hand from handles 2 and 3 the spiral needle 12 with a string and with a drive of its rotation is placed, in the middle department and on the other hand from handles various kinds of the surfaces fixing stitched tissues, directing movement of a spiral needle and a jack 17 for reception of the sharp end of a needle 12 are placed.

For rotation of the holder 15 (FIG. 21) a tail part of a spiral needle 12, or the cylinder 28 with an internal thread (FIG. 22) in which the spiral needle 12 is placed, and also for rotation of a jack 17 in which the sharp end of a spiral needle is fixed after suture, rotation devices, shown on FIG. 6 and FIG. 7 are used. For rotation of the holder 15 in the cylinder 25 in these devices the end of a rotating shaft coming forward in process of rotation or a core is provided. Diameter of the end of a shaft or core should be less, than diameter of the holder 15.

It is possible to use other devices transferring rotation of the handle 24 to holder 15 or jack 17 under necessary angle, for example, drive shaft or devices with an adjustable angle of rotation disclosed in RU 2284160.

The suture in this variant is practically the same as in the previous variants: the clip on a stitched site of a tissue is imposed. The holder 15 incorporates to the cylinder 25. Rotation of the handle 24 begins the movement of the spiral needle 12 stitching a tissue. The sharp end of a spiral needle leaves tissues and gets in a jack 17. When the spiral needle should be taken out from tissues by the sharp end of a needle, the cylinder 25 is disconnected from the holder 15 and incorporates to a jack 17.

Rotation of the handle 24 helps to take out the spiral needle 12 from tissues. The stitched string is stretched and its ends are fixed, as is specified earlier.

Hollow Spiral Needle

Two variants of a hollow spiral needle use are possible.

Figure 24:
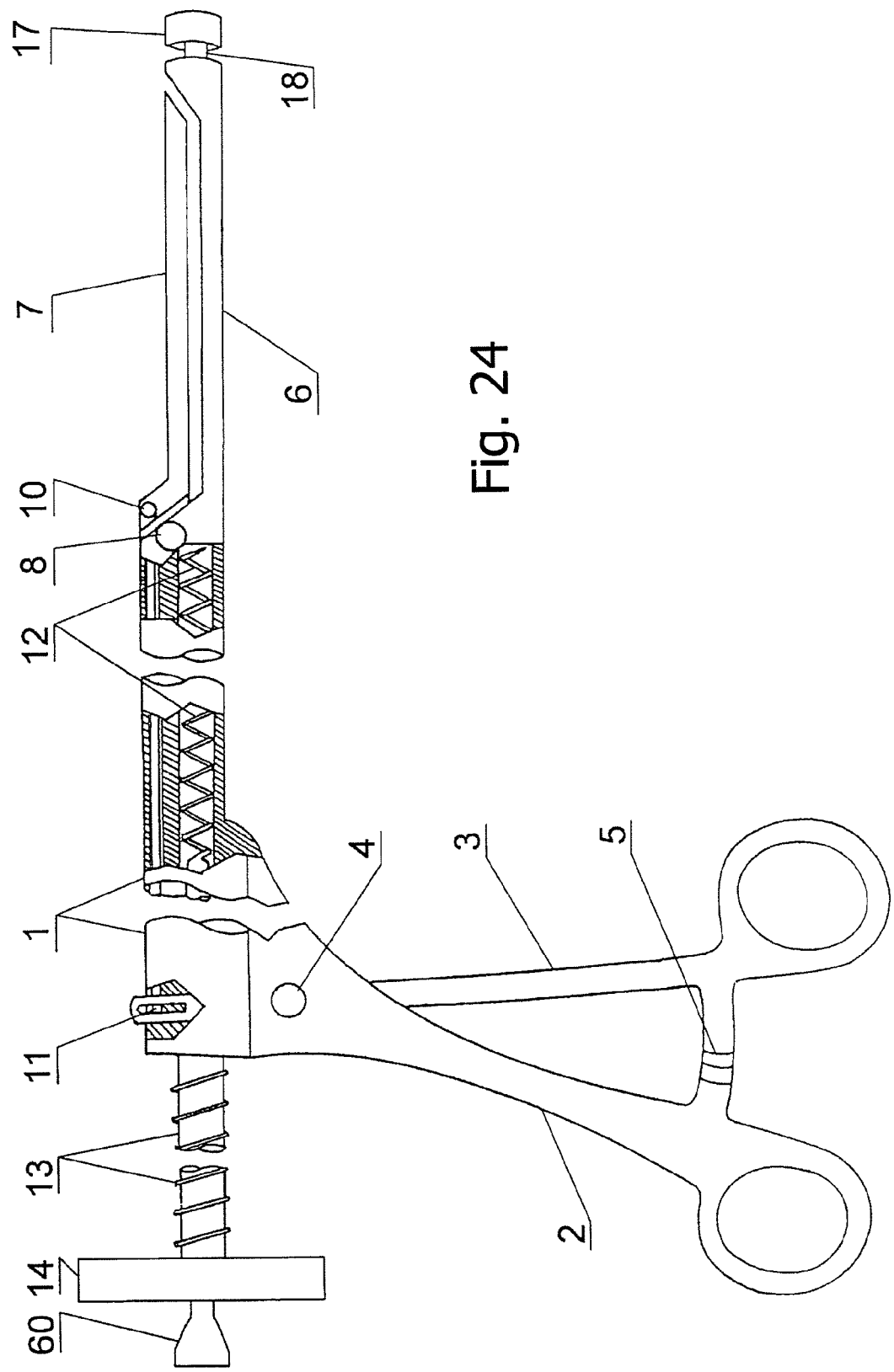
FIG. 24—a variant of the sewing device with the hollow spiral needle moving inside of tightening gripping jaws.
Figure 25:
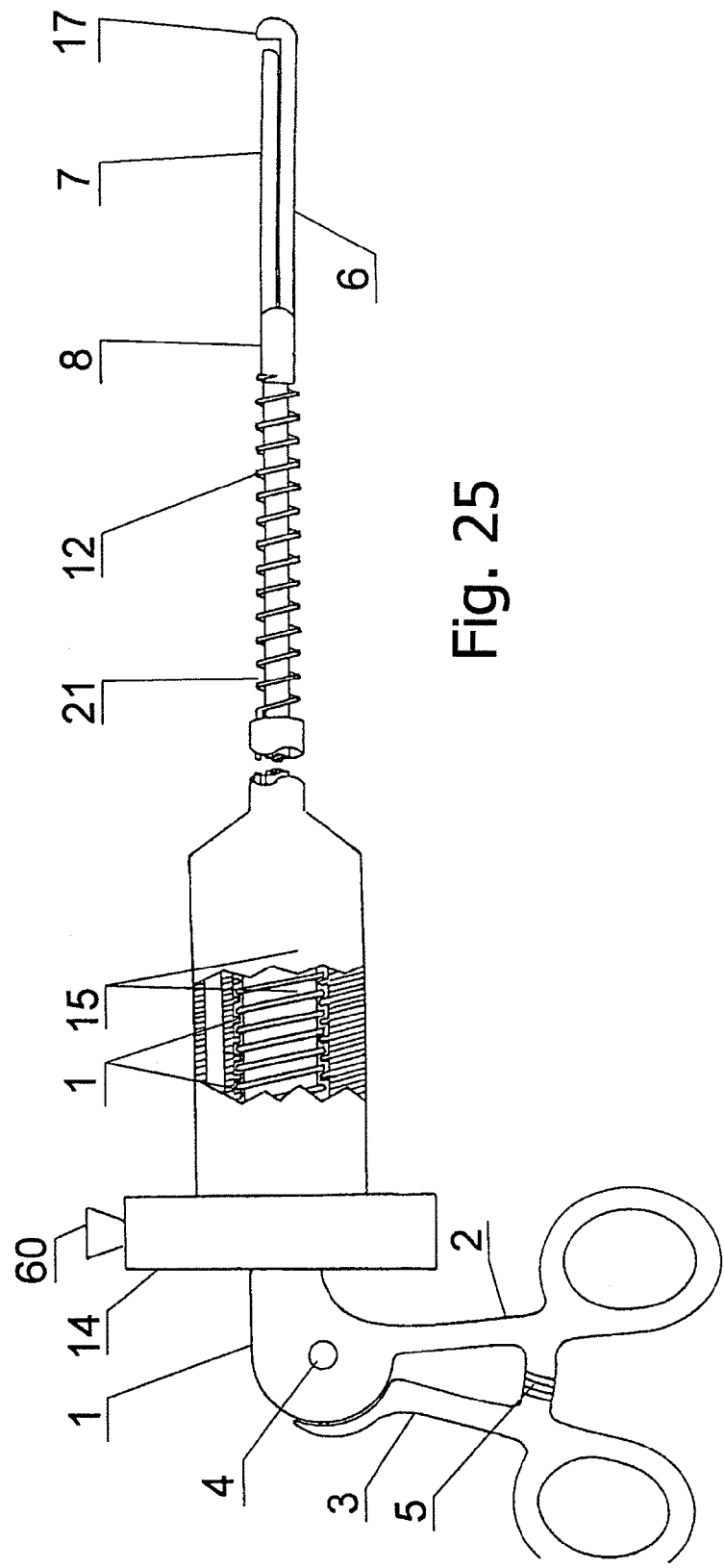
FIG. 25—a variant of the sewing device with the hollow spiral needle moving on an external surface of gripping jaws.

The first variant, in which the taking out of a string from a hollow spiral needle under pressure of air or a liquid is provided, is presented on FIGS. 24 and 25. The string can be taken out from a hollow needle also with mandrin. This variant is similar to a variant shown on FIG. 1 and a variant shown on FIG. 10. The difference of this variant is rigid connection of the screw 13 with a hollow spiral needle 12.

Inside of the screw 13, also as well as inside of a spiral needle 12, there is a hollow channel through which air or a liquid under the certain pressure are pushed in a hollow needle with a string to push out a string from a hollow needle. In the center of the handle 14 there is a bell 60 into which the syringe with a liquid or air is inserted or the end of a hose from the device with compressed air is inserted. On the distal end of a motionless gripping jaws 6 there is a jack 17 in which gets and where is fixed the end of the string pushed out of the hollow spiral needle.

After that the hollow spiral needle 12 by the rotation of the handle 14 in a underside comes back in a starting position—from working gripping jaws 6 and 7 and stitched tissues back in the device body of 1. The string remains in tissues in the form of a winning round seam. The sewing device is opened and taken out. The ends of a string are fixed, as noted above.

In the second version the string located inside of a hollow spiral needle, is solidly fixed in the sharp end of a needle.

Practically, this version is similar to the versions shown on FIGS. 1, 10, 24 and 25.

After tissues suture the sharp end of a hollow spiral needle 12 with the string fixed in it gets in a jack 17 in which the sharp end is fixed and broken off on in advance stipulated line. Then this jack 17 with the sharp end of a needle is extended from tissues together with the end of a string fixed in the sharp end of a needle. In this case, as well as in previous, the string is stretched through a spiral needle remaining in tissues, not touching the tissues. A part of a spiral needle remaining in tissues is taken out from tissues as a result of return rotation of the directing screw 13.

In this variant diameter of a hollow needle is less, than in the previous variant.

About advantages and disadvantages of these variants it is told above.

Thus, the presented versions of sewing device for tissues suture by a twinning round seam with a spiral needle with modern strings, facilitate and accelerate surgical interventions, automating a part of work of the surgeon, and reduce a trauma of stitched tissues to a minimum. Similar arrangements can be applied also in other areas.

The invention claimed is:

1. A sewing device for making a mechanical encircling stitch, containing
    a body having a spiral needle and gripping jaws for fixing sewn sites of tissue;
    the spiral needle, having a sharp end and being capable of rotational and forward motion, connected with a drive of its motion; said spiral needle comprising at least two full coils and being an atraumatic needle or a hollow needle with a thread-containing cavity;
    said gripping jaws being located on the distal end of the body and being adapted for management of their relative position, the gripping jaws having rounded external surfaces permitting sliding of a spiral needle on said surfaces or the gripping jaws comprising an indent or hollow wherein the spiral needle can move so that said spiral needle can move along said gripping jaws, at least, for all the length of a spiral, portion of said spiral needle
    the distal end of one of the gripping jaws including a jack for fixing the sharp end of said spiral needle, said jack being capable of rotation on the distal end and being connected with said distal end by a demountable connection.

2. The device as claimed in claim 1, wherein the distal end of a gripping jaw, bearing the jack, is unbent, and on an internal surface a second gripping jaw, the surface being slanted for direction of the sharp end of the spiral needle to the jack.

3. The device as claimed in claim 1, wherein at least one of the gripping jaws comprises clamping plates having openings for passage of spiral needle coils are located on facing surfaces of said gripping jaws.

4. The device as claimed in claim 3, wherein one of clamping plates is mobile, and the surface of clamping plates intended for interaction with sewn tissues, is covered by a thin layer of a biocompatible material.

5. The device as claimed in claim 1, wherein the drive of the spiral needle motion is in the form of a device established in the body and capable of rotation of a cylinder with an internal thread, in which the spiral needle is located.

6. The device as claimed in claim 1, wherein the drive of the spiral needle motion is connected with a needle by a demountable connection by means of a flexible rod or rotary hinge mechanism, wherein any one of said flexible rod, and rotary hinge mechanism is adapted for selective connection with a needle.

7. The device as claimed in claim 6, wherein the rotary hinge mechanism has a changeable turning angle.

8. The device as claimed in claim 1, wherein the spiral needle is an atraumatic needle containing 2-4 coils, and the drive of the spiral needle motion is in the form of, at least, one rotary roller, whose axis is parallel to an axis of the spiral needle and which cooperates by its lateral surface with said coils to impart a rotary movement to said spiral needle.

9. The device as claimed in claim 8, comprising one or two rollers having a screw flute with step equal or multiple to the distance between coils of a spiral needle.

10. The device as claimed in claim 8, comprising one or two rollers having on the surface parallel cylindrical flutes, located one from another on the distance equal to distance between coils of a spiral needle.

11. The device as claimed in claim 8, comprising three or four smooth rollers which are distributed on a circle of a spiral needle and have been drawn in to it.

12. The device as claimed in claim 1, comprising a mechanism of rotation of the jack for fixing the sharp end of the spiral needle, said mechanism being located on a shaft, parallel to an axis of the spiral needle and is connected with an external surface of a jack by a tooth gearing.

13. The device as claimed in claim 1, wherein the spiral needle is a hollow needle with a thread located in its cavity, the device further comprising a means for removal of thread, after full tissue suture, from a cavity of a spiral needle by a mandrin, compressed air or a liquid.

14. The device as claimed in claim 1, wherein the spiral needle is a hollow needle with a thread located in its cavity, the thread being fixed in the sharp end of the needle, the sharp end of the needle having a weakened zone for separation of the sharp end of the needle fixed in a jack with a thread from a body of the needle thereby permitting removal of the needle from the stitched tissue by a reverse motion of the needle motion drive.

15. The device as claimed in claim 1, wherein the needle is an atraumatic one, the device being supplied by a mechanism for drawing out and tensioning of a thread through one, two or greater number of turns of said atraumatic spiral needle.

\* \* \* \* \*